United States Patent
Lucey et al.

(10) Patent No.: US 11,684,261 B2
(45) Date of Patent: Jun. 27, 2023

(54) SYSTEMS AND METHODS FOR MONITORING IMPLANTABLE DEVICES FOR DETECTION OF IMPLANT FAILURE UTILIZING WIRELESS IN VIVO MICRO SENSORS

(71) Applicant: OrthoDx Inc., Hilton Head Island, SC (US)

(72) Inventors: John D. Lucey, Weaverville, NC (US); Paul Ierymenko, Asheville, NC (US)

(73) Assignee: OrthoDx Inc., Hilton Head Island, SC (US)

( * ) Notice: Subject to any disclaimer, the term of this patent is extended or adjusted under 35 U.S.C. 154(b) by 134 days.

(21) Appl. No.: 17/204,077

(22) Filed: Mar. 17, 2021

(65) Prior Publication Data

US 2022/0061668 A1 Mar. 3, 2022

Related U.S. Application Data

(62) Division of application No. 15/805,726, filed on Nov. 7, 2017, now Pat. No. 10,980,419.

(Continued)

(51) Int. Cl.
*A61B 5/00* (2006.01)
*A61B 8/08* (2006.01)
(Continued)

(52) U.S. Cl.
CPC ............ *A61B 5/0031* (2013.01); *A61B 5/112* (2013.01); *A61B 5/4851* (2013.01);
(Continued)

(58) Field of Classification Search
CPC ..... A61B 5/0031; A61B 5/112; A61B 5/4851; A61B 8/0833; A61B 34/10; A61B 5/686;
(Continued)

(56) References Cited

U.S. PATENT DOCUMENTS

| | | | |
|---|---|---|---|
| 3,868,565 A | 2/1975 | Kuipers | |
| 4,454,881 A | 6/1984 | Huber et al. | |

(Continued)

FOREIGN PATENT DOCUMENTS

| | | | |
|---|---|---|---|
| EP | 3058865 A1 | 8/2016 | |
| JP | 2009279161 A | 12/2009 | |

(Continued)

OTHER PUBLICATIONS

"International Search Report and Written Opinion for PCT/US2017/060358 dated Feb. 5, 2018, 11 pages.".

*Primary Examiner* — Sunita Reddy
(74) *Attorney, Agent, or Firm* — Myers Bigel, P.A.

(57) ABSTRACT

An implantable position detecting system is configured to detect a position of an implantable device with respect to a body structure. The system includes at least one proximity measuring transducer configured to be implanted on the body structure a distance from the implantable device, the at least one proximity measuring transducer being configured to receive energy from an external electromagnetic field generated by an external sensing interface, wherein the at least one proximity sensor is configured to emit an emitted signal responsive to the electromagnetic energy and to receive distance information comprising a sensing signal that is responsive to the distance from the implantable device.

17 Claims, 9 Drawing Sheets

Related U.S. Application Data

(60) Provisional application No. 62/418,701, filed on Nov. 7, 2016.

(51) Int. Cl.
| | | |
|---|---|---|
| *A61B 5/11* | (2006.01) | |
| *A61B 34/10* | (2016.01) | |
| *A61F 2/32* | (2006.01) | |
| *A61F 2/46* | (2006.01) | |
| *A61B 8/00* | (2006.01) | |
| *A61B 17/16* | (2006.01) | |
| *A61B 17/17* | (2006.01) | |

(52) U.S. Cl.
CPC .......... *A61B 8/0833* (2013.01); *A61B 34/10* (2016.02); *A61F 2/32* (2013.01); *A61F 2/4657* (2013.01); *A61B 5/686* (2013.01); *A61B 8/0875* (2013.01); *A61B 8/56* (2013.01); *A61B 17/1666* (2013.01); *A61B 17/1746* (2013.01); *A61B 2560/0219* (2013.01); *A61B 2562/028* (2013.01); *A61F 2250/0001* (2013.01)

(58) Field of Classification Search
CPC ..... A61B 8/0875; A61B 8/56; A61B 17/1666; A61B 17/1746; A61B 2560/0219; A61B 2562/028; A61F 2/32; A61F 2/4657; A61F 2250/0001
USPC .................................. 128/897–899
See application file for complete search history.

(56) References Cited

U.S. PATENT DOCUMENTS

| | | |
|---|---|---|
| 4,849,692 A | 7/1989 | Blood |
| 4,945,305 A | 7/1990 | Blood |
| 7,521,842 B2 | 4/2009 | Tucker et al. |
| 8,915,866 B2 | 12/2014 | Nycz |
| 8,939,153 B1 | 1/2015 | Reicher et al. |
| 9,198,654 B1 | 12/2015 | Reicher et al. |
| 9,360,294 B2 | 6/2016 | Ashe |
| 2004/0127787 A1 | 7/2004 | Dimmer et al. |
| 2004/0167390 A1 | 8/2004 | Alexander et al. |
| 2005/0027192 A1 | 2/2005 | Govari et al. |
| 2006/0241397 A1 | 10/2006 | Govari et al. |
| 2007/0013540 A1 | 1/2007 | Altmann et al. |
| 2008/0077016 A1* | 3/2008 | Sparks ................ A61B 5/0031 600/459 |
| 2009/0069866 A1 | 3/2009 | Farbarik et al. |
| 2009/0157145 A1 | 6/2009 | Cauller |
| 2009/0187120 A1 | 7/2009 | Nycz |
| 2009/0216113 A1 | 8/2009 | Meier et al. |
| 2010/0015918 A1 | 1/2010 | Liu et al. |
| 2010/0023092 A1 | 1/2010 | Govari et al. |
| 2010/0161004 A1 | 6/2010 | Najafi et al. |
| 2010/0331663 A1 | 12/2010 | Stein |
| 2011/0288379 A1 | 11/2011 | Wu |
| 2011/0319755 A1* | 12/2011 | Stein ................ A61B 5/4851 623/18.11 |
| 2012/0190989 A1 | 7/2012 | Kaiser et al. |
| 2013/0071828 A1 | 3/2013 | Lang et al. |
| 2013/0217998 A1 | 8/2013 | Mahfouz et al. |
| 2014/0303489 A1 | 10/2014 | Meier et al. |
| 2015/0019135 A1 | 1/2015 | Kacyvenski et al. |
| 2015/0045700 A1 | 2/2015 | Cavanagh et al. |
| 2015/0257799 A1 | 9/2015 | Janna et al. |
| 2016/0270927 A1 | 9/2016 | Zellmer et al. |
| 2016/0302721 A1 | 10/2016 | Wiedenhoefer et al. |
| 2016/0310066 A1 | 10/2016 | Wiedenhoefer et al. |
| 2017/0086674 A1* | 3/2017 | Keefer ................ A61B 5/4504 |
| 2017/0095667 A1 | 4/2017 | Yakovlev et al. |
| 2017/0319096 A1 | 11/2017 | Kaiser et al. |
| 2018/0036115 A1 | 2/2018 | Smirnov |
| 2018/0125365 A1* | 5/2018 | Hunter ..................... A61B 5/01 |
| 2019/0076033 A1 | 3/2019 | Sweeney et al. |
| 2019/0150835 A1* | 5/2019 | Bae ......................... H02J 50/15 |
| 2020/0281471 A1* | 9/2020 | Hunter ................ A61N 1/3702 |

FOREIGN PATENT DOCUMENTS

| | | |
|---|---|---|
| WO | 2007061890 A2 | 5/2007 |
| WO | 2011022418 A2 | 2/2011 |
| WO | 2016154230 A1 | 9/2016 |

\* cited by examiner

SYSTEMS AND METHODS FOR MONITORING IMPLANTABLE DEVICES FOR DETECTION OF IMPLANT FAILURE UTILIZING WIRELESS IN VIVO MICRO SENSORS

RELATED APPLICATION

This application is a divisional application of U.S. application Ser. No. 15/805,726 filed Nov. 7, 2017, which application claims priority to U.S. Provisional Application Ser. No. 62/418,701, filed Nov. 7, 2016, the disclosures of which are hereby incorporated by reference in their entireties.

FIELD OF THE INVENTION

The present disclosure is generally directed to sensing systems for monitoring mammalian orthotic implants and more specifically to prosthesis assessment for early detection of implant failure.

BACKGROUND

In total hip replacement (THR) both the femoral head and acetabulum are replaced with prosthetic components typically made of materials such as stainless steel, titanium, ceramic, or cobalt chromium. Cartilage is replaced by a durable polyethylene or other suitable low friction material. The patient's original femoral head and acetabulum are removed and/or modified; the remaining bone is carefully sculpted to interface with the prosthesis.

THR has a very high success rate. Today, cement is typically no longer used to fix the implant within the bone and a successful THR is characterized by robust ossification whereby the patient's bone bonds with specially prepared porous regions of the implant. After a period of recuperation, normal functionality is reestablished and loadbearing forces are transmitted between bone and implant without pain or discomfort. Some patients report that they often forget they have a prosthesis.

However, some patients do experience problems after a THR. In some cases, ossification never occurs or is insufficient. Ossification sometimes progresses normally and the patient reports success, yet after a time, the pain and discomfort returns. Such pain is often due to loosening of the implant because of osteolysis, which may have a septic or aseptic cause. Unfortunately, sometimes after a patient complains persistently of pain, the surgeon performs surgery in order to replace the hip replacement, and during the surgery discovers there was nothing wrong and the pain was idiopathic.

There exist a variety of means and procedures for assessing an implant. The patient's synovial fluid and blood may be examined for changes characteristic of infection. X-rays, sonograms, MRI, etc. may be used to image the interface of implant and bone. However, none of these options reliably provide a sufficiently accurate early indication of implant loosening.

Thus there is a need for a diagnostic tool that provides a reliable indication of implant loosening so remedial steps can be taken before the degradation has created significant complications.

The book "Quaternions and Rotation Sequences", by Jack B Kuipers, published in 1999 by Princeton University Press, presents a review of the mathematics of coordinate frames, their properties and applicable transformations.

U.S. Pat. No. 3,868,565 proposes an arrangement of three mutually orthogonal transmitting antennas used to detect the full position of an arrangement of three mutually orthogonal receiving antennas. One problem is that there is more than one position that produces the same characteristic signal in the detecting coils, which is overcome by nutating the transmitted field. A series of iterative readings that gradually converge upon the result are performed.

U.S. Pat. No. 4,454,881 proposes an arrangement of three mutually orthogonal transmitting antennas and three mutually orthogonal receiving antennas "where measurement of signals received from the transmitting antennas in combination with one known position or orientation parameter produces nine parameters sufficient to determine the position and orientation of the receiving antennas." The measurement is made quickly in one computational pass. Concise mathematics are presented.

U.S. Pat. Nos. 3,868,565 and 4,454,881 have two deficiencies. The first deficiency is that electromagnetic fields are absorbed by bodily tissues, which causes errors of measurement in vivo. The second deficiency is that the oscillating fields used for measurement give rise to eddy currents within any nearby electrically conductive objects, which generate parasitic alternating magnetic fields that distort the transmitted field and cause errors in the measurement.

U.S. Pat. Nos. 4,849,692 and 4,945,305 propose a location measurement system utilizing pulsed direct-current magnetic fields. Bodily tissues and non-ferrous conductive metals do not interact with a substantially steady magnetic field in a way that causes errors in the measurement. By holding the magnetic field steady for a time sufficient for eddy currents induced in conductive materials to die down to substantially zero, accurate location measurements through bodily tissues and in the presence of non-ferrous prosthesis metal are made possible. Concise mathematics and operational algorithms for cancelling noise, etc., are presented.

In addition, the above configurations require active electronics to be connected by wires at both transmitter and receiver, and are therefore not directly suitable for long-term implantation in a patient.

U.S. Pat. No. 9,360,294 proposes a full position measuring system having transmitters to energize the system with both a DC and an AC magnetic field, a marker responsive to the transmitted signals, and receivers responsive to a second harmonic signal generated by the marker. The marker however cannot accurately measure the position of an implanted prosthesis.

U.S. Pat. No. 7,521,842 B2 and U.S. Patent Publication No. 20100015918A1 propose an apparatus and method for wireless near field magnetic data and power transfer. A magnetoelectric (ME) device including a piezoelectric layer bonded to and sandwiched by one or two magnetostrictive layers is proposed and may also include a bias magnet layer to improve sensitivity. The resulting structure can be driven at resonance to emit an electromagnetic field, e.g., to provide a transmitter, and the structure can be monitored to detect an electromagnetic field, e.g., to provide a receiver. Like a coil transducer, a magnetoelectric transducer's coupling is sensitive to the vector of the coupling field so it can be used to measure an orientation parameter. It differs from a coil transducer in that for a given coupling, an ME device may be made smaller than a coil transducer. A magnetoelectric transducer can be manufactured to have a natural resonant frequency and a very high Q factor, (>100). The natural resonant frequency is defined by the geometry of the device, thus several magnetoelectric transducers of different geometry can be deployed together, operated simultaneously and distinguished one from another by frequency.

SUMMARY OF EMBODIMENTS OF THE INVENTION

In some embodiments, an implantable position detecting system is configured to detect a position of an implantable device with respect to a body structure. The system includes at least one proximity measuring transducer configured to be implanted on the body structure a distance from the implantable device, the at least one proximity measuring transducer being configured to receive energy from an external electromagnetic field generated by an external sensing interface, wherein the at least one proximity sensor is configured to emit an emitted signal responsive to the electromagnetic energy and to receive distance information comprising a sensing signal that is responsive to the distance from the implantable device.

In some embodiments, the at least one proximity sensor is configured to transmit the distance information to the external sensing interface.

In some embodiments, the at least one proximity measuring transducers comprises a magnetoelectric transducer having a resonant frequency, and the external sensing interface is configured to transmit energy to the magnetoelectric transducer to drive the magnetoelectric transducer at the resonant frequency in an activation period, and the magnetoelectric transducer is configured to emit the emitted signal as an electromagnetic field and then to sense the electromagnetic field post activation in a sensing period, wherein the external sensing interface or the at least one proximity sensor is further configured to determine a distance from the proximity measuring transducer to the implantable device based on variations in the sensed electromagnetic field.

In some embodiments, the system includes a biometric marker, the biometric marker comprising the at least one proximity measuring transducer and at least one additional component selected from the group consisting of an energy storage device, a data storage structure, a microcontroller, a sensor and a transceiver.

In some embodiments, the sensor is selected from the group consisting of an accelerometer, a magnetometer and a temperature sensor.

In some embodiments, the microcontroller is configured to collect data from the at least one proximity measuring transducer or the sensor.

In some embodiments, the at least one additional component comprises an energy storage device, and the external sensing interface is configured to generate an alternating magnetic waveform to drive the magnetoelectric transducer, and the magnetoelectric transducer is configured to convert the alternating magnetic waveform to an electrical signal and to store energy from the alternating magnetic waveform on the energy storage device to thereby provide a wireless power receiver.

In some embodiments, the at least one additional component comprises the sensor, the microcontroller and the transceiver, the microcontroller being configured to receive data from the sensor and to send data by the transceiver to the external sensing interface or an external computer system.

In some embodiments, the proximity measuring transducer comprises an electromagnetic tank circuit having at least one coil element and at least one capacitor element connected in a resonant circuit configuration.

In some embodiments, the implantable device comprises at least one conductive component.

In some embodiments, the at least one proximity measuring transducer comprises at least one implantable proximity measuring transducer. The system further includes the external sensing interface having at least one external proximity measuring transducer configured to further detect a position of the at least one implantable proximity measuring transducer and the implant.

In some embodiments, the at least one external proximity measuring transducer comprises at least three orthogonal external proximity measuring transducers.

In some embodiments, the at least three orthogonal external proximity measuring transducers comprise magnetoelectric transducers configured to generate an electromagnetic field and to sense an electromagnetic field responsive to a position of the implantable device and the at least one internal proximity measuring transducer.

In some embodiments, the at least one proximity measuring transducer comprises an ultrasound transducer and an ultrasound receiver, and the ultrasound transducer is configured to emit an ultrasound signal in a direction toward the implantable device and the ultrasound receiver is configured to receive an echo signal from the implantable device. The at least one proximity measuring transducer is configured to determine a distance to the device responsive to the echo signal.

In some embodiments, a method of monitoring a position of an implantable device with an implantable position detecting system is provided. The implantable position detecting system is configured to detect a position of an implantable device with respect to a body structure. The method includes providing at least one proximity measuring transducer configured to be implanted on the body structure a distance from the implantable device; transmitting energy from an external electromagnetic field generated by an external sensing interface to the at least one proximity measuring transducer; emitting, by the at least one proximity measuring transducer, an emitted signal responsive to the electromagnetic energy, receiving distance information at the at least one measuring transducer, the distance information comprising a sensing signal that is responsive to the distance from the implantable device; and determining if the implantable device is properly positioned based on the electromagnetic field.

In some embodiments, the step of determining if the implantable device is properly positioned is carried out with an empirically-based model of actual clinical experience.

In some embodiments, the empirically-based model of actual clinical experience comprises a database of distance measurements carried out over time and a likelihood that a change in distance value resulted in implant detachment.

In some embodiments, receiving distance information comprises detecting a first measurement when the implant is substantially free of weight loading and detecting a second measurement when the implant is weight loaded, and the step of determining if the implantable device is properly positioned is based on a difference between the first and second measurement.

In some embodiments, the at least one proximity sensor is configured to transmit the distance information to the external sensing interface.

In some embodiments, the at least one proximity measuring transducers comprises a magnetoelectric transducer having a resonant frequency, and the external sensing interface is configured to transmit energy to the magnetoelectric transducer to drive the magnetoelectric transducer at the resonant frequency in an activation period, and the magnetoelectric transducer is configured to emit the emitted signal as an electromagnetic field and then to sense the electromagnetic field post activation in a sensing period. The external sensing interface or the at least one proximity sensor is further configured to determine a distance from the proximity measuring transducer to the implantable device based on variations in the sensed electromagnetic field.

In some embodiments, the system includes a biometric marker, the biometric marker comprising the at least one proximity measuring transducer and at least one additional component selected from the group consisting of an energy storage device, a data storage structure, a microcontroller, a sensor and a transceiver.

In some embodiments, the sensor is selected from the group consisting of an accelerometer, a magnetometer and a temperature sensor.

In some embodiments, the microcontroller is configured to collect data from the at least one proximity measuring transducer or the sensor.

In some embodiments, the at least one additional component comprises an energy storage device, and the external sensing interface is configured to generate an alternating magnetic waveform to drive the magnetoelectric transducer, and the magnetoelectric transducer is configured to convert the alternating magnetic waveform to an electrical signal and to store energy from the alternating magnetic waveform on the energy storage device to thereby provide a wireless power receiver.

In some embodiments, the at least one additional component comprises the sensor, the microcontroller and the transceiver, the microcontroller being configured to receive data from the sensor and to send data by the transceiver to the external sensing interface or an external computer system.

In some embodiments, the proximity measuring transducer comprises an electromagnetic tank circuit having at least one coil element and at least one capacitor element connected in a resonant circuit configuration.

In some embodiments, the implantable device comprises at least one conductive component.

In some embodiments, the at least one proximity measuring transducer comprises at least one implantable proximity measuring transducer, and the system further includes the external sensing interface having at least one external proximity measuring transducer configured to further detect a position of the at least one implantable proximity measuring transducer and the implant.

In some embodiments, the at least one external proximity measuring transducer comprises at least three orthogonal external proximity measuring transducers.

In some embodiments, the at least three orthogonal external proximity measuring transducers comprise magnetoelectric transducers configured to generate an electromagnetic field and to sense an electromagnetic field responsive to a position of the implantable device and the at least one internal proximity measuring transducer.

In some embodiments, the at least one proximity measuring transducer comprises an ultrasound transducer and an ultrasound receiver, and the ultrasound transducer is configured to emit an ultrasound signal in a direction toward the implantable device and the ultrasound receiver is configured to receive an echo signal from the implantable device, the at least one proximity measuring transducer being configured to determine a distance to the device responsive to the echo signal.

BRIEF DESCRIPTION OF THE DRAWINGS

The accompanying drawings, which are incorporated in and constitute a part of the specification, illustrate embodiments of the invention and, together with the description, serve to explain principles of the invention.

DETAILED DESCRIPTION OF EMBODIMENTS OF THE INVENTION

Figure 1:
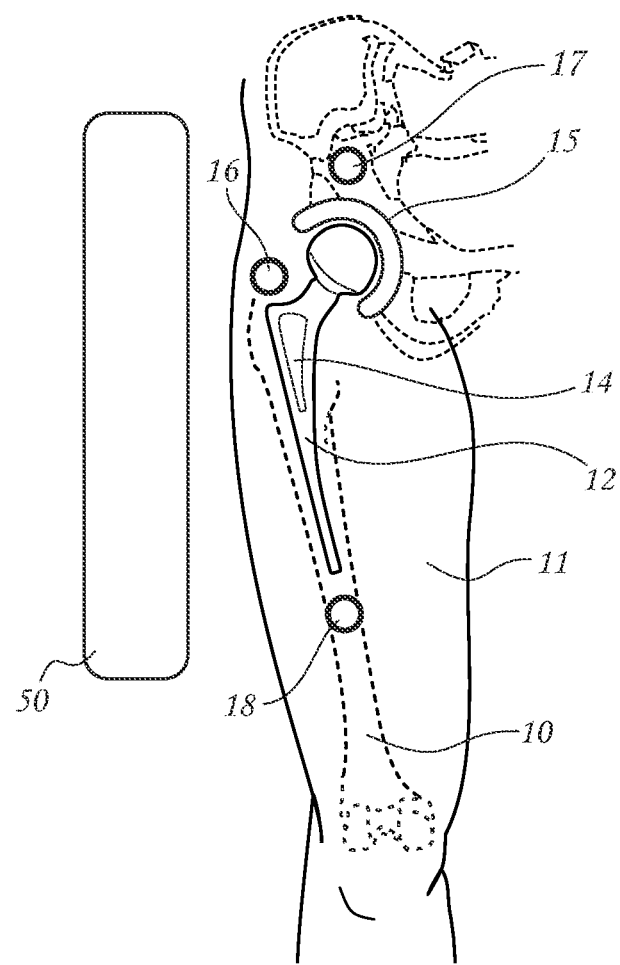
FIG. 1 is a block diagram illustrating an example system for evaluating prosthesis stability according to some embodiments of the invention.

The present invention now will be described hereinafter with reference to the accompanying drawings and examples, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under." The device may be otherwise oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only unless specifically indicated otherwise.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

The present invention is described below with reference to block diagrams and/or flowchart illustrations of methods, apparatus (systems) and/or computer program products according to embodiments of the invention. It is understood that each block of the block diagrams and/or flowchart illustrations, and combinations of blocks in the block diagrams and/or flowchart illustrations, can be implemented by computer program instructions. These computer program instructions may be provided to a processor of a general purpose computer, special purpose computer, and/or other programmable data processing apparatus to produce a machine, such that the instructions, which execute via the processor of the computer and/or other programmable data processing apparatus, create means for implementing the functions/acts specified in the block diagrams and/or flowchart block or blocks.

These computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagrams and/or flowchart block or blocks.

The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions/acts specified in the block diagrams and/or flowchart block or blocks.

Accordingly, the present invention may be embodied in hardware and/or in software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system.

The computer-usable or computer-readable medium may be, for example but not limited to, an electronic, optical, electromagnetic, infrared, or semiconductor system, apparatus, or device. More specific examples (a non-exhaustive list) of the computer-readable medium would include the following: an electrical connection having one or more wires, a portable computer diskette, a random access memory (RAM), a read-only memory (ROM), an erasable programmable read-only memory (EPROM or Flash memory), an optical fiber, and a portable compact disc read-only memory (CD-ROM).

The term "full position" as used herein signifies the location and orientation of an object in a first frame of reference from the vantage point of a second frame of reference, i.e., a measurement defining position in six degrees of freedom, namely, motion of translation in three coordinate directions (location as used herein) and rotational motion about three coordinate axes (orientation as used herein), location being commonly defined by X, Y and Z linear coordinates referring to three mutually perpendicular directions and orientation being commonly defied by pitch, roll and azimuth angular coordinates about three mutually perpendicular axes usually coincident with the three mutually perpendicular directions.

Certain embodiments disclosed herein provide for a system for measuring the in vivo placement of a prosthesis. For example, one system includes at least two sensors placed into the body of a patient near an implanted prosthesis (e.g., a total hip replacement implant) and a method employing the at least two sensors that includes activating the sensors and receive wireless data from the sensors and analyzing the data from the sensors to determine a position of the implanted prosthesis. Multiple positions of the implanted prosthesis are determined over time, for example while the patient is walking, to determine any micro movement of the implanted prosthesis. In this fashion, early detection of unstable implanted prosthesis is possible.

Although embodiments according to the present invention are described herein with reference to a human total hip replacement ("THR") implanted prosthesis, it should be understood that the disclosure may be applied to assess other prosthetic implants elsewhere in the body such as the knee.

In some embodiments, an implantable position detecting system is configured to detect a position of an implantable device with respect to a body structure. The system may include at least one proximity measuring transducer configured to be implanted on the body structure a distance from the implantable device. The proximity measuring transducer is configured to receive energy from an external electromagnetic field generated by an external sensing interface. The proximity sensor is configured to emit an emitted signal responsive to the electromagnetic energy and to receive distance information comprising a sensing signal that is responsive to the distance from the implantable device. The proximity sensor may emit the emitted signal after receiving energy from the external electromagnetic field. The proximity measuring transducer can transmit a signal indicating the distance to the implantable device to the external sensing interface. The proximity measuring transducer can convey energy to a storage device, such as a battery. The energy is received from an electromagnetic field generated by the external sensing interface, for example, and can be stored to operate additional sensors, store data and to emit signals, such as an electromagnetic field or ultrasound signal for detecting a distance to the implant. Such a system may provide a single distance measurement, which can be measured over time, as opposed to a full position location system, or the transducers may be provided as part of a system that may take full position measurements. Distance measurements may be made once it is believed that an implantable device is successfully implanted and monitored over time, with or without a load, to determine if proper implantation is maintained or if a failure has occurred.

Although the magnetoelectric transducers may be used to measure distance directly as described above, in some embodiments, a self-resonant magnetoelectric transducer may serve as a passively responding indicator of a position as measured by an external device. An external alternating polarity field drives a receiving magnetoelectric transducer at resonance and then the external field is turned off or brought to zero. The transducer will continue emitting at its natural resonant frequency, transmitting an electromagnetic field that can be monitored for the purpose of locating the transducer. Three such magnetoelectric transducers tuned to three different frequencies can be fixed in a mutually orthogonal configuration to form a passive wireless marker device that can be first energized and then monitored during its free-ringing decay interval to calculate the full position of the marker device. Examples of self-resonant magnetoelectric transducers are described in U.S. Pat. No. 7,521,842.

In some embodiments of the instant invention, the full position marker device described above may utilize a resonant tank circuit comprising a coil and a capacitor instead of a self-resonant magnetoelectric transducer in a mutually orthogonal array of three instances to form a passive wireless marker device that can be first energized and then monitored during a ringing decay interval to derive the full position of the marker device.

In some embodiments of the invention, a self-resonant magnetoelectric transducer serves as wireless power receiver for transferring energy to a local energy storage device and thereby provides power to an active in vivo device. The active in vivo device transmits data as an analog signal or as a digital code to an external receiver, the transmission being made via the same magnetoelectric transducer now operated as a transmitter.

In some embodiments, the active in vivo device is equipped with three orthogonally oriented magnetometers and is capable of reporting its full position to an external device wirelessly even when close to eddy current field interference from nearby conductive objects. Full position is measured by receiving a succession of three magnetic pulses each pulse being long enough for eddy currents to subside or to be canceled as is described in the U.S. Pat. Nos. 4,849,692 and 4,945,305.

In some embodiments, a self-resonant magnetoelectric transducer, an energy storage device, a microcontroller to govern operations and store and formulate the data for transmission and one or more magnetometers constitute an active wireless biometric marker. Frequency discrimination of communication via differently tuned magnetoelectric transducers allows several such devices to be deployed in the same field space and to simultaneously report individual data. Different measurement devices reading for example temperature or acceleration may replace or augment the magnetometer function and all can be powered by the local storage device. A housing or coating may be provided for an assembly of a magnetoelectric transducer, an energy storage device, a microcontroller to govern operations and store and formulate the data for transmission and a variety of miniaturized and/or mems sensors having different sensing functions, i.e., an accelerometer, one or more magnetometers, a thermometer, etc., and the housed or coated assembly can be implanted in vivo. Such an assembly is referred to as a "wireless biometric marker" in discussions that follow.

In a variation of the wireless biometric marker, a resonant tank circuit including a coil and parallel capacitor is an alternative structure which may be physically larger but otherwise functionally equivalent to a self-resonant magnetoelectric transducer. In like manner, various other components of a wireless biometric marker may be replaced by substantially equivalent components, for example the magnetometer function may be performed by a GMR device, a coil magnetometer, a Hall-effect sensor, etc.

Those skilled in the art will be familiar with a range of suitable sensors.

In some embodiments of the instant invention, full position sensing of at least one in vivo wireless biometric marker is performed as specified in U.S. Pat. No. 9,360,294, which provides for a very small, passive wireless implantable full position marker.

Some embodiments of the invention remotely sense the proximity of an implant by monitoring energy loss in a resonant system electromagnetically coupled to the conductive implant and generating eddy currents therein. As is commonly the case, the implant must be made of conductive material but no special modification of the implant is required. The position of the implant is calculated by processing data from a number of points of measurement distributed about the region of the prosthesis. Thus the position of any prosthesis made of conductive metal can be measured and tracked. This capability allows these embodiments to be retrofitted to patients who already have a prosthesis.

In some embodiments of the instant invention, the prosthesis is itself equipped with one or more instances of a wireless biometric marker and the full position of the prosthesis is thereby measured and tracked. Both the femoral stem implant and the acetabular cup may be so equipped and each THR component measured and tracked independently of the other.

In some embodiments, at least one wireless marker device is solidly fixed to the bone of the femur onto or close to the greater trochanter of a patient. In some embodiments, a second wireless device marker is solidly fixed to the bone of the femur somewhere between the knee and the distal end of the prosthesis, either by inserting the marker into the hollow of the femur or by attaching the marker to the surface of the femur. Having two full position markers on the femur for establishing the full position of the femur implant portion of the full hip replacement prosthesis, and further having a system external to the patient for wirelessly driving and interrogating the full position markers and the position of the implant, the relative position of the implant and the femur can now be measured and tracked over time as the patient walks on a treadmill.

In some embodiments of a total hip replacement diagnostic system, at least one wireless biometric marker is solidly fixed to the pelvic bone above the acetabular cup. This biometric marker will perform proximity detection of the metallic portion of the acetabular cup relative to its position on the pelvic bone. This biometric marker may also perform other functions such as measuring acceleration, etc.

In some embodiments of the total hip replacement diagnostic system, one or more wireless biometric markers are adapted to be fixed to the pelvic bone and located close but not in contact with the acetabular cup, at least one biometric marker is fixed to the femur on the greater trochanter close to but not touching the prosthetic implant and a second biometric marker may be fixed to the femur distally just below but not touching the end of the implant stem. The prosthetic components themselves may have wireless biometric markers integrated within. A series of measurements is made and the prosthetic components are located with respect to markers. Unusual motions indicative of degradation may be detected between the acetabular cup and the pelvic bone, and or between the femoral component and the bone of the femur.

In some embodiments, there is a sensing interface external to the patient that communicates with and or collects data from in vivo sensors. The subsystem may also transmit power to remote in vivo devices.

The external sensing interface also has inputs for the collection of ancillary data such as from a sensor responsive to the contact of a patient's foot with a treadmill which may be a strain gauge, piezoelectric, conductive, or another suitable sensor.

The external sensing interface or individual components thereof may be worn by the patient, for example by being strapped to the patient's thigh, or in some embodiments the external sensing interface may be entirely disconnected from but in close proximity to the patient's thigh.

In further embodiments, the data streams collected by the sensors are processed to extract clinically significant features. The signal processing may include the step of autocorrelation of a sequential series of similar events such as gait cycles of a patient's walk on a treadmill, the step of selecting a subset of cycles above a correlation threshold, and of further processing steps which may include stretching a cycle slightly in time to align key features of each cycle within a record of cycles, for example adjusting all heel strikes to occur at a first same record index and making all toe lifts occur at a second same record index. Such "stretching" algorithms are well understood in the field of signal processing for audio and video data streams. By selecting and fitting the most similar strides one to another and averaging the sensor readings over many such strides, accuracy and precision are improved and the extrinsic noise and power line hum, the intrinsic noise of the sensing system and the stochastic component of walking motion are reduced. Fourier analysis may also be performed on the resulting single averaged gait cycle to better identify qualitative and quantitative changes in motion relative to a previously acquired averaged gait cycle measurement. Once the data is collected and made available to a generalized signal processing mathematical environment such as Matlab for example, novel useful transformations and data visualizations can be freely experimented with. The data may be presented graphically and/or numerically with color coding to indicate areas where for example the relative motions between markers and a prosthesis exceed predetermined thresholds.

In some embodiments, at least one series of gait cycles is recorded with the patient walking in place on a treadmill while wearing strapped to the thigh an external sensing interface. A first series is recorded with the patient walking in place on a treadmill and as the thigh is moved in the pattern of a normal walk, the leg supports the patient's full weight during each loadbearing phase of the gait cycle. A second series of data may be recorded with the patient walking in place on a treadmill but with body weight supported by a set of stationary crutches so that the thigh is moved in the pattern of a normal walk but only minimal weight is actually placed on the leg. In some embodiments, an external sensing interface is alternatively deployed in a stationary position relative to the treadmill and as close as possible but not in contact with the patient's thigh. Variations on the type of motion are expected as some patients may have difficulty walking. For example, the patient may merely transfer his weight cyclically between his leg and a set of crutches so that the prosthesis is subjected to a cyclically varying load without the patient actually walking. A different type of cyclic motion may be more effective than another type for detecting loosening of prosthetic components.

Reference is now made to FIG. 1 of the drawings which illustrates a patient's thigh 11 with a total hip replacement undergoing instrumented assessment. Prosthetic implant 12 performs the function of the femoral head and is seated within the hollow core of femur wireless biometric marker 18 and is fixed to the distal end of the femur ideally 5 mm to 20 mm from the distal end of the implant by a suitable fastener such as a screw, or by being inserted into the open cavity of the femur and fixed in place by interference. Wireless biometric marker 16 is fixed to the femur close to or upon the greater trochanter, 5 mm to 20 mm away from the metal of the implant. The implant will typically have a zone 14 having a porous or sintered surface where a solid bond with the surrounding bone of the thigh normally forms by ossification during the recovery period after THR surgery.

A wireless biometric marker 17 is fixed to the pelvic bone above the acetabular cup 15 and ideally 5 mm to 20 mm from the metal of the cup. As the pelvic bone moves relative to the femur during walking, wireless biometric marker 17 establishes the orientation of the pelvic reference frame separately from the orientation of the reference frame of the femur, which is established by markers 16 and 18. In most of the discussion that follows, the operations are explained in terms of the markers associated with the femoral component but the same explanation applies to markers in any reference frame within which is found any kind of metallic implant, including the pelvic reference frame and the acetabular cup.

FIG. 1 also shows in block form the external sensing interface 50 deployed outside of the patient but in close proximity to the implant. The external sensing interface 50 may take many forms including that of an apron like device worn by the patient and strapped to the thigh, a freestanding adjustable device to be deployed as close to the patient as possible but not touching the patient, or a combination of wearable and freestanding electronics. The external sensing interface may generate electromagnetic fields to interrogate or charge the markers 16, 17 and 18 and may also send/receive data from the markers 16, 17 and 18.

Figure 2:
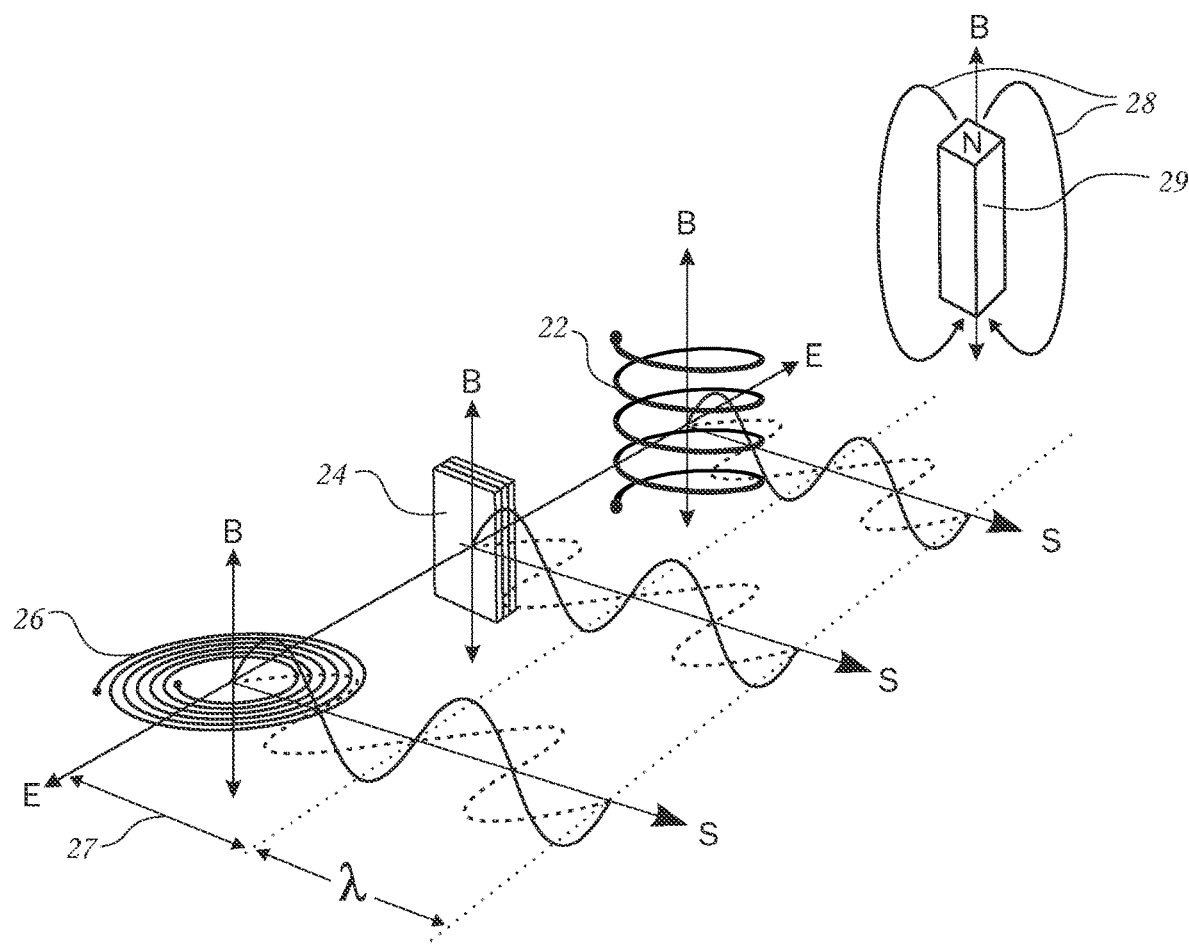
FIG. 2 is a block diagram illustrating an example correspondence between different dipole radiators according to some embodiments of the invention.

Reference is now made to FIG. 2 which illustrates dipole transducers in the form of solenoid coil 22, magnetoelectric device 24, and spiral coil 26 oriented to produce equivalently oriented electromagnetic fields. The vertical magnetic fields B are represented propagating as a solid sinewave while the dashed horizontal sinewaves represent the accompanying electric field, E, as would obtain were the transducers driven by an sinusoidally oscillating current. Poynting, (not "pointing"), vector S indicates the direction of propagation. Magnetoelectric transducer 24 operates as described in U.S. Patent Publication No. 2010/0015918A1 included herein by reference. It is noted that the "magnetoelectric" effect has been known and researched since at least 1926 when the term was coined by Nobel laureate Peter Debye. (Note regarding Poynting: the coincidence between the discovers name and the vector quantity is remarkable: The Poynting vector represents the directional energy flux density of an electromagnetic field in W/m2. "Pointing" is often misused in the literature instead of "Poynting", even by experts. It "points" in the direction of propagation).

FIG. 2 also shows a permanent bar magnet dipole 29 oriented the same as the other dipoles and surrounded by static magnetic field 28. As field 28 is not oscillating, there is only an external magnetic field and no external electric field. Such a stationary magnetic field penetrates the human body without distortion, absorption or reflection. Furthermore, no eddy currents are generated in conductive materials such as an implant. Once a magnetic field is modulated in amplitude or polarity, an external electric field arises that is subject to absorption loss, while the undulating or oscillating magnetic field induces eddy current losses in conductive materials. These effects present difficulties for in vivo communication which increase with the oscillation frequency. A range of low frequencies exists where the wavelength is very long compared to the length of the human body and the aforementioned losses are small. In general, the longer the wavelength, the more its behavior approaches that of a static field.

In FIG. 2, transducers 22, 24, 26 may range in size from a millimeter to a few centimeters. The dipole transducers and the wavelengths of waveforms illustrated in FIG. 2 are not drawn to the same scale and merely illustrate the electromagnetic propagation vector. For example, a frequency of 100 kHz useful for in vivo communication and proximity sensing has a wavelength of 300 meters, therefore if drawn to scale the waveform portion traversing the length of a human body would appear as a straight line and the drawing itself would span a kilometer.

Due to the large ratio of the electromagnetic wavelength to the length of a human body, all communication and sensing interactions between in vivo devices and the external sensing interface take place well within the near field region 27 indicated in FIG. 2. In the near field, absorption and eddy current losses can be sensed as a loading effect at the transmitter. Absorption losses are low for low frequencies. Thus, electromagnetic full position sensing, inductive proximity sensing, near field magnetic communication and wireless power transfer are permitted.

Figure 3:
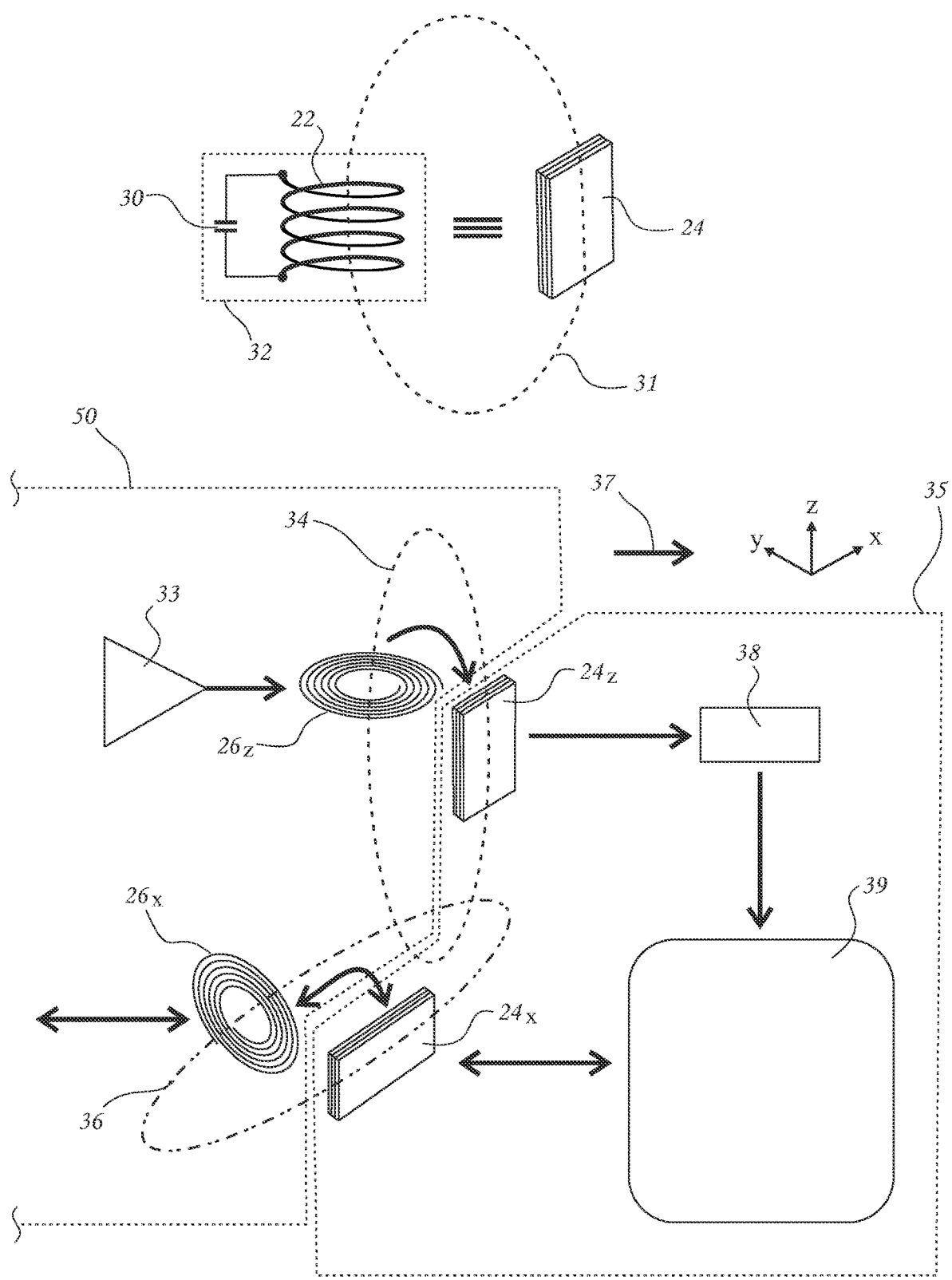
FIG. 3 is a block diagram illustrating example wireless communication and power transfer according to some embodiments of the invention.

Reference is now made to FIG. 3, which shows magnetoelectric transducer 24, constructed of a central piezoelectric layer for converting electromotive force (EMF) into a strain transmitted mechanically to bonded outer layers of magnetostrictive material which respond to strain by generating a magnetic dipole field. It also works in the other direction, generating EMF in response to a magnetic dipole field. The magnetoelectric structure always exhibits a strong (Q>100) self-resonance at relatively low frequencies. Its specific frequency is physically determined by its size, shape, mass, materials, construction and immediate environment and so is not easily changed. Magnetoelectric transducer 24 can be made smaller than 1 cm in its long axis making it suited to in vivo applications and when so made may be mechanically resonant at frequency in the range of 100 kHz to 300 kHz and well-suited to near field magnetic communication.

FIG. 3 also shows a tank circuit 32 having a coil 22 in parallel with a capacitor 30. Tank circuit 32 is resonant at frequency. Tank circuit 32 can be tuned to the same resonant frequency as magnetoelectric transducer 24, making the tank circuit roughly equivalent in function. However, coil 22 and therefore tank circuit 32 would have to be larger than magnetoelectric transducer 24 to achieve the same effectiveness of coupling, making an LC tank circuit a less practical circuit element for in vivo use.

FIG. 3 also shows spiral coils 26 $x$ and 26$z$ which can operate efficiently across a wide range of frequency. This property makes an electromagnetic coil better suited for coupling use in the external sensing interface subsystem 50, which must adjust its coupling frequencies according to the self-resonant frequencies of a patient's particular in vivo magnetoelectric transducers.

The dark arrows 37 shown in FIG. 3 illustrate the unidirectional flow of power and the bidirectional flow of information.

FIG. 3 also shows a portion of external sensing interface 50 having a driver 33 for driving coil 26$z$ with an alternating current waveform tuned to the self-resonant frequency of magnetoelectric transducer 24$z$. The magnetic axis of coil 26$z$ is oriented to that of transducer 24$z$ thus coupling the transducers via magnetic field 34. Magnetoelectric transducer 24$z$ receives the alternating magnetic waveform and converts it to an electrical signal which conveys energy from driver 33 to energy storage system 38 which may employ a capacitor, a battery, or any other energy storage device to accumulate and store the conveyed energy and provide electrical power for a device 39. The device 39 may include any kind of sensor, microcontroller, memory, etc. and typically requires electrical power. In some embodiments, the device 39 will include at least the functions of proximity sensing, the receiver portion of a full position sensing system, a microcontroller and a half duplex receiver/driver. The device 39 may receive data, for example instructions on when and at what rate to perform measurements, and may generate data from its sensors. The device 39 includes a half-duplex circuit for receiving a carrier and demodulating data from magnetoelectric transducer 24$x$ during a first time period and for driving during a second time period transducer 24$x$ with a carrier tuned to the self-resonant frequency of transducer 24$x$ and modulated with outgoing data. External sensing interface 50 has further circuitry not shown which connects to spiral transducer 26x and performs a corresponding half duplex function for exchanging data with other connected circuits not shown. Magnetoelectric transducer 24z is configured to operate at a self-resonant frequency different to that of magnetoelectric transducer 24x. Field 36 couples the transducers 26x and 24x and field 34 couples the transducers 26z and 24z. No coupling occurs where fields 34 and 36 are orthogonally oriented. Therefore, the power transfer channel is isolated from the wireless data transfer channel in two ways, first by operating at a different carrier frequency and second by being orthogonally oriented.

FIG. 3 also shows elements 24z, 38, 39, and 24x enclosed within wireless biometric marker 35 which is adapted for prolonged implantation in vivo and may also be adapted to be secured to the bone such as the patient's femur by having a hole for a screw, or other attachment facility. Magnetoelectric transducers 24z and 24x are orthogonally oriented but may be positioned flat on the same plane for fabrication on a flat substrate. Accordingly, fastening biometric marker 35 to a patient's femur establishes a coupling orientation which may either be known or discovered for a patient in order to align the position external sensing interface 50 for coupling adequately to supply power and communicate data. Two axes must be considered.

Marker 35 may be positioned to align transducer 24z to the vertical, but then transducer 24x must also be positioned at a suitable rotation around the vertical axis for coupling to external sensing interface 50 which due to the patient's motion may be positioned at the patient's side rather than behind or in front of the patient. This constraint is manageable, but it would be better if it could be removed entirely. A single constraint of maintaining a vertical position would be better and no constraint would be best.

It will be understood by those skilled in the art that an indication of coupling could be presented to the clinician to indicate the quality of coupling to the external sensing interface 50 as an aid to positioning the sensing interface.

It will be understood by those skilled in the art that it is also possible, with an increase in complexity, to have two half duplex channels interleaved to provide simultaneous bidirectional data transfer. Unidirectional power transfer to the in vivo system could be provided by appropriately switching between one or the other magnetoelectric transducer being externally driven during ongoing bidirectional communication.

Figure 4:
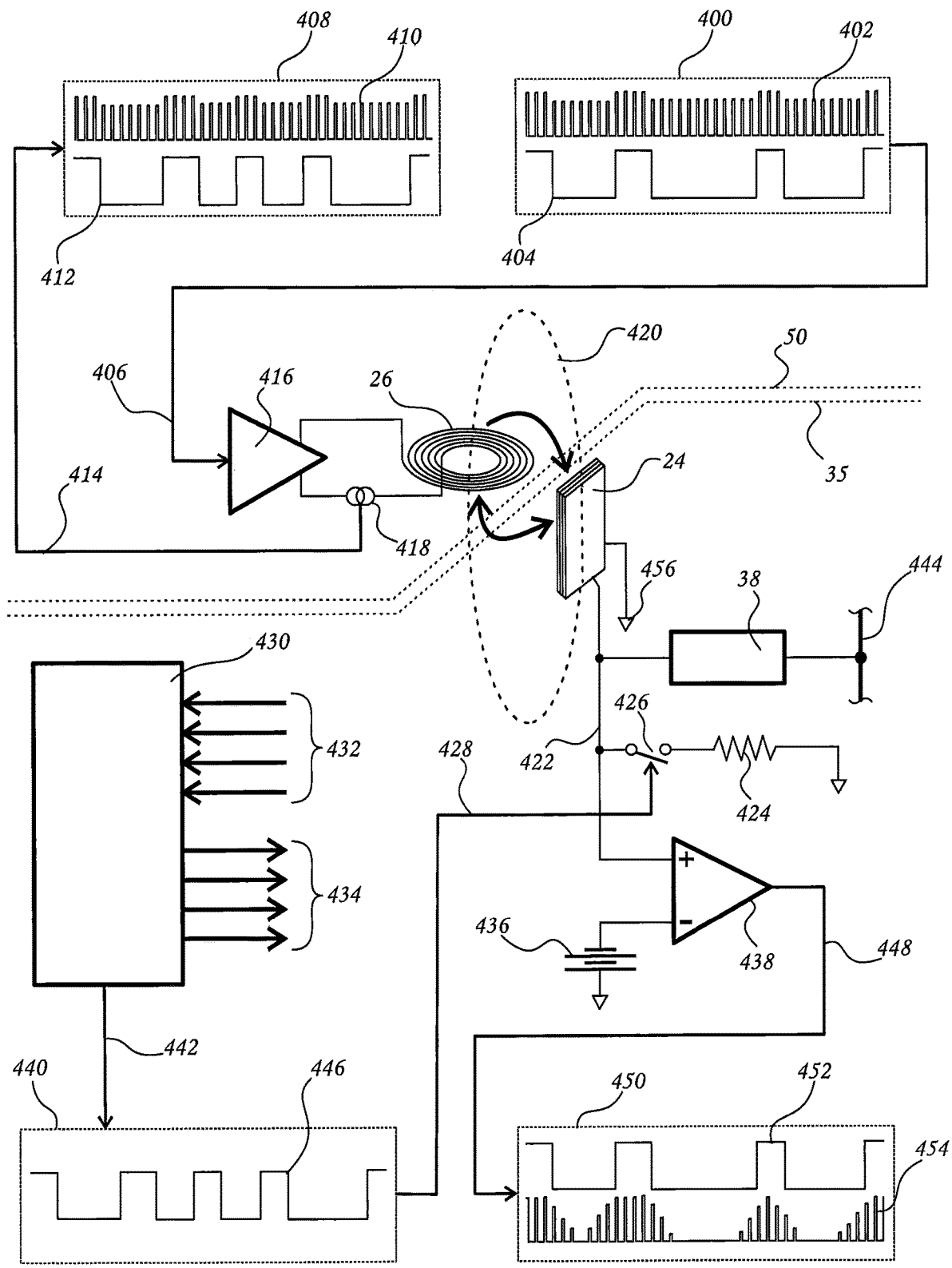
FIG. 4 is a block diagram illustrating example bidirectional wireless communication occurring simultaneously and on the same channel as unidirectional wireless power transfer according to some embodiments of the invention.

Reference is now made to FIG. 4 which uses symbols to illustrate the simultaneous transfer of power and half duplex data between interface 50 and a biometric marker 35. In embodiments of the invention, all functions which can more efficiently be performed digitally will be performed by a microcontroller or other similarly capable device. For clarity, in FIG. 4 some of these functions are represented as analog functions.

When the external interface is first energized, it enters a calibration mode and executes an algorithm designed to discover the natural self-resonant frequency of magnetoelectric transducer 24. This may be performed in several different ways. For example, a carrier frequency may be swept from the lowest expected frequency towards the highest expected frequency while monitoring current sensor 418. When an increase in current is registered, the carrier frequency can be nutated by a search algorithm to find the peak current which indicates the frequency of greatest coupling between coil 26 and magnetoelectric transducer 24. This frequency is then set as the carrier frequency. This calibration process may be controlled by the system microcontrollers executing suitable firmware. Once calibration is complete, the marker 35 awaits further instructions from interface 50. One possible next step is for interface 50 to send instructions to marker 35 determining which sensors are to be activated next and in what mode of operation. This is an example of a system preparing to acquire data and will be familiar to those skilled in the art. However, various operations may be conducted in different orders.

A second of many ways to initialize the communication frequency would be to ping magnetoelectric transducer 24 with a sufficiently sharp magnetic impulse causing it to ring and therefore transmit a decaying sinusoidal frequency signature which could be sensed by interface 50 using either an auxiliary sensor, (not illustrated), or by using spiral inductor 26 as a receiver. Given at least two cycles of ringing, the natural resonant frequency of transducer 24 can be measured and the communication frequency initialized thereby.

During half duplex communication, there is a first transmitting timeframe at interface 50 co-temporal with a receiving time frame at marker 35 and a second transmitting timeframe at marker 35 co-temporal with a receiving timeframe at interface 50. The sequence of such first and second timeframes constitutes one full-duplex communication cycle. The duration of the first and second timeframes is not necessarily equal.

During the first transmitting timeframe, data 404 from message buffer 400 is transmitted to message buffer 450 where it appears as data 452. During the second transmitting timeframe, data 446 from message buffer 440 is transmitted to message buffer 408 where it appears as data 412. Both time frames make use of the unidirectional carrier wave having frequency matched to the self-resonant frequency of transducer 24 which is transmitted from coil 26 by the field 420 and received by magnetoelectric transducer 24. This process will now be described in detail.

During the first transmitting timeframe, a data set 404 provided by a microcontroller function of interface 50, not illustrated in FIG. 4 for clarity, modulates the amplitude of a carrier waveform according to the binary value of the data resulting in modulated carrier waveform 402. This amplitude modulation may be shallow having peaks at full amplitude and troughs just slightly but sufficiently lower in amplitude to encode the information. The resulting modulated carrier 402 is conveyed via node 406 to coil driver 416 which is a subcircuit having functions to drive the spiral inductor transducer 26 therefrom. Driver 416 drives coil 26 with a voltage waveform representing the modulated carrier which produces a modulated near-field magnetic flux carrying data and power to magnetoelectric transducer 24.

During the same first time frame, transducer 24 receives the modulated magnetic carrier and converts it to an electrical waveform analog available on node 422. Comparing and conditioning subcircuit 438 compares the analog modulated carrier waveform at 422 against a threshold voltage 438 which may be fixed or may be provided by microcontroller 430. After the comparison, an envelope detection function recovers the data signal 452 which is sufficiently identical to the transmitted signal 404 to convey the data without error. Waveform 454 represents the topmost portion of the waveform on node 422 from which data 452 is extracted and is provided to illustrate a nuance of this circuit's behavior. Magnetoelectric transducer 24 may have resonance factor Q as high or higher than 100. Such a strong resonance will have a filtering effect, smoothing out the amplitude variations of the transmitted amplitude modulated carrier, removing high-frequency components and turning step transitions in amplitude into gradients. This effect will limit the bandwidth of communication significantly more than implied by a carrier in the range of 200 kHz. The bandwidth may be increased by loading transducer 24 resistively as is done by the PFC in subcircuit 38 and thus damping the resonance of the magnetoelectric transducer 24. This may diminish but not eliminate the filtering effect. However, even under the conditions described, data transfer rates of several thousand baud should be realized. This nuance of operation and other similar complexities can be overcome using modulation and demodulation techniques known to those skilled in the art.

During the second transmitting timeframe, transmission of data from marker 35 to interface 50 is effected by propagating information backwards through the continuously driven unidirectional carrier. Data message 440 is delivered by microcontroller 430 through node 442. Data set 446 is an example of such a message and is sent datum by datum to node 428 to control the opening and closing of switch 426 according to the datum polarity. Switch 426 connects and disconnects a load 424 to node 422 which results in a load variation pattern that carries the information in data message 440. Since all of the energy at node 422 comes from driver 416 via transducer 26, the load variation pattern can be sensed as a pattern of current changes by current sensor 418 occurring as driver 416 acts to maintain a constant carrier voltage amplitude on coil 26. Data sequence 446 is thus recovered as data sequence 412 after demodulating waveform 410 provided by current sensor 418. This is how data message 440 from marker 35 is wirelessly propagated back through field 420 to data message 408 of interface 50 in the presence of a continuous unidirectional carrier transmission in the other direction.

Simultaneously with the communication activities described above, energy harvesting, storage and supply subsystem 38 captures electrical power from the waveform at node 422, stores it in any suitable energy buffer such as a battery or a capacitor, and produces a suitably regulated voltage source to power bus 444, which is understood to provide power to the electronics within marker 35. Within subsystem 38, the energy may be harvested using an energy efficient method also having desirable impedance characteristics. As will be understood by those skilled in the art, a power-factor-corrected (PFC) switch mode stage using synchronized rectification captures energy efficiently and continuously from source transducer 24 via node 422 at which can be made to appear as a continuous resistive load which does not mask or interfere with the amplitude modulation on the carrier. The power demands of the electronics within marker 35 will fluctuate as different circuit features are enabled and disabled; therefore, the subsystem 38 buffers and filters these fluctuations so they are not expressed at node 422 in any way that causes data errors.

The switch 426 and resistor 424 are shown in FIG. 4 as analog elements. However, in a more efficient design the load modulating function they provide would instead be effected by modulating the energy harvesting behavior of subsystem 38 in such a way as to produce the same load modulation. The advantage of this more sophisticated method would be that instead of wasting some power in resistor 424, this power would be stored and used productively as part of the overall power flow into power bus 444 of marker 35.

Further details of driver 416, subsystem 38 and other subcircuits of FIG. 4 will be readily inferred by those skilled in the art and are omitted here for brevity. For example, the output stage of driver 416 may be an MOSFET H-bridge stage, etc.

The system of communication described above is also capable of full-duplex communication. Since interface 50 knows what it is transmitting and marker 35 knows what it is transmitting, and since the transmissions can be superposed without loss of information upon the single field 420, it is possible for both the first and second time frames to operate concurrently. Each receiver will recover the unknown transmission from the nonlocal transmitter by subtracting out the superposed known local transmission in its received signal.

FIG. 4 shows a representation of microcontroller 430 with input lines 432 and output lines 434. Although four lines of each are illustrated it is well-known that microcontrollers are available having far more or far fewer such lines and furthermore having such lines where a line 432 is internally reprogrammable to be a line 434 or even a greater number of different purposed lines.

In the highly conceptual representation shown in FIG. 4, microcontroller input lines 432 would be analog signal lines and microcontroller 430 would include a suitably capable analog-to-digital converter subcircuit for digitizing these lines. Output lines 434 may be either analog or digital lines for controlling the sequence of measurements, for supplying calibrated offsets or other precise gradients, etc. Lines 434 could also be I^2C or SPI communication links, and other intelligent devices could communicate complex data with microcontroller 430. This is all current and well known and suitable microcontroller devices are available.

In a biometric marker 35 the analog inputs 432 will connect to outputs from a variety of sensors including at least one magnetometer, the possible form of magnetometer including one or more giant magnetostrictive resistors ("GMR"), one or more Halleffect sensors or coils responsive to magnetic fields including various known fluxgate magnetometers, or other types of magnetometers. The ideal magnetometer will report, when driven with a field generating array capable of generating fields of any orientation, respond with measurements sufficient for establishing both location and orientation of the magnetometer in relation to the reference frame of the field, i.e. full position sensing.

Figure 5:
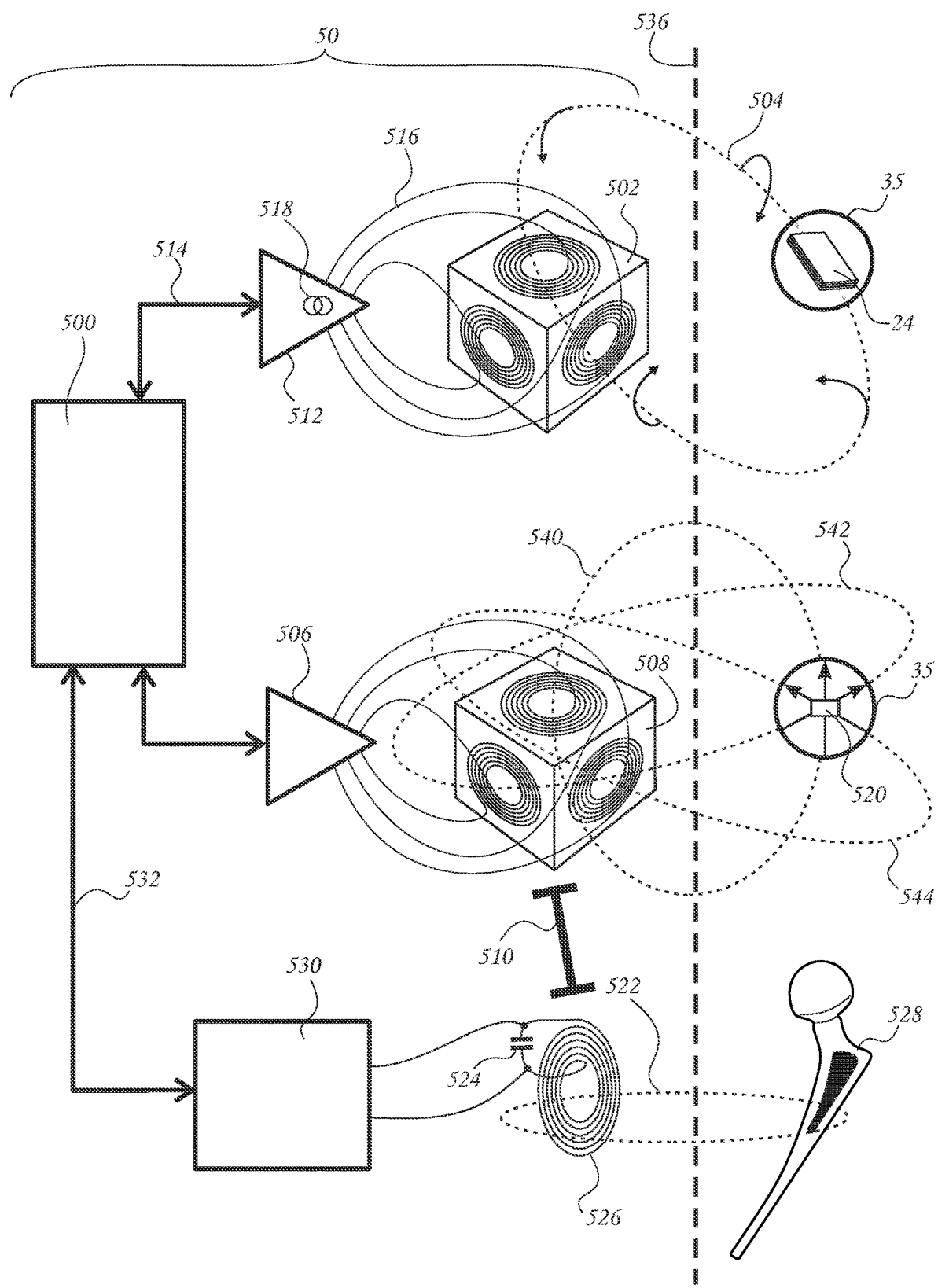
FIG. 5 is a block diagram illustrating example power transfer and data exchange between elements located outside of the body and elements located in vivo according to some embodiments of the invention.

Reference is now made to FIG. 5 which shows configurations for coupling for communication and power transfer, for measurement of full position, and for inductive proximity measurement. Line of demarcation 536 separates in vivo components from external components comprising external sensing interface 50. Microcontroller 500 is programmed to instantiate the various functions and activities of interface 50 and a portion of its functionality is illustrated.

An aspect of establishing communication and power transfer with a wireless biometric marker 35 involves aligning the coupling field 504 with an axis of sensitivity of magnetoelectric transducer 24 illustrated for emphasis within a biomarker 35. Automatized alignment is now described. Transponder driver 512 has circuits for receiving data in either analog or digital form over data bus 514 from microcontroller 500 and for transforming this data into three sets of drive signals connected by six wires, of which wire 516 is an example, to coil set 502 including three inductive coils fixed in a mutually orthogonal orientation. Coils are shown as flat spiral coils but may be of different geometry such as a solenoid. Transponder driver 512 combines the functions of three instances of driver 416 and three channel current sensor 518 combines the functions of three instances of current measurement device 418. Under the control of microcontroller 500, by driving one, two, or all three coils with appropriate amplitudes of waveforms, transponder 502 can emit a magnetic dipole field polarized in any direction. During initialization the magnetic dipole field 504 is gradually revolved through all possible orientations while driven repeatedly with an event frame including first an impulse event which transmits an impulse over a field 504 to biometric marker 35, followed immediately by a sensing event for detecting the ringing echo from highly resonant transducer 24. The circuitry of marker 35 is arranged to not damp the ringing of transducer 24 during this initialization procedure, however all other magnetoelectric transducers within the same marker 35 are damped by shorting during this initialization procedure. The responses to full position measurement events are processed and stored as survey of coupling coefficients mapped against impulse field vectors. Once all orientations of field 504 have been thus examined, microcontroller 500 determines which orientation will couple most effectively for ongoing power transfers and communications. Microcontroller 500 also measures the frequency of the ringing echo which establishes the communication frequency for a particular magnetoelectric transducer 24. After this, the system proceeds with half duplex for full-duplex communication and continuous power transfer as previously described with reference to FIG. 4, except driver 416, current sensor 418 and single coil 24 are replaced in the description by transponder driver 512 and triaxial transponder 502 which, once initialized by the foregoing procedure, serve the same functions.

FIG. 5 also shows a triaxial driver 506 connected to triaxial transducer 508 and adapted to perform full position measurement of wireless biometric node 35, in this instance illustrated emphasizing its internal magnetometer 520. The coils within triaxial transducer 508 are adapted to emit pulsed DC magnetic fields of sufficient length to eliminate eddy current effects. Driver 506, triaxial transducer 508, and multi axial magnetometer 520 operate as described with reference to functionally similar components in U.S. Pat. Nos. 4,849,692 and 4,945,305. Microcontroller 500 gathers data from repetitive full position measurements for storage and further analysis. Although U.S. Pat. Nos. 4,849,692 and 4,945,305 discuss sequentially emitting a pulsed magnetic field from one or two of three orthogonally arranged transducers; the type of magnetometer used for receiving and measuring the pulses is not specified. Those skilled in the art will know that accurate miniaturized magnetometers are currently available. For example, the function of magnetometer 520 may be satisfied by the MLX90365 component manufactured by the Melexis company of Belgium is an integrated triaxial magnetometer using the Hall-effect and having internal processing to sharpen and format results. NVE corporation of the USA has giant magnetoresistive sensor components for use in magnetometers. Lorentz force MEMS magnetometers are also available. Those skilled in the art will know that for certain magnetometer technologies, other ongoing transmissions may be suspended from the external interface 50 and other sources for an amount of time to make an undisturbed multi-axes magnetometer measurement. This and other considerations of routine engineering are omitted herein for clarity.

FIG. 5 further shows proximity sensing subsystem 530 connected to microcontroller 500 over data bus 532. The functionality of subsystem 530 is conceptually identical to the functionality of available Texas Instruments integrated circuit LDC1000, the datasheet of which is included herein by reference. In the datasheet, proximity to a metallic object may be measured either by the change in inductance of an inductive transducer, or in terms of an implied damping term Rp which is a function of the eddy current losses in the metallic object being detected. Rp may be resolved with sufficient precision. The frequency of operation is set by the inductance of spiral coil 526 and the capacitance 524 and is selected to easily penetrate the body. Subsystem 530 may actually be implemented using LDC1000 integrated circuit, or an equivalent functionality can be realized using other components in conjunction with microcontroller 500.

In FIG. 5, symbol 510 symbolizes a rigid connection between triaxial transducer 508 and proximity sensing coil 526 ensuring that these are fixed within the same frame of reference. This makes it possible to translate the full position measurement and the proximity measurement both made relative to external components 508 and 526 into a proximity measurement of the prosthesis component 528 relative to the magnetometer 520.

In embodiments of the invention, there may be several copies of this proximity measuring aspect comprised by subsystem 530, coil 526, capacitor 524 also rigidly fixed within the same reference frame as triaxial transducer 508. The several copies may be deployed around prosthetic implant 528 from different directions to capture different components of motion of the implant. The use of flat spiral inductors facilitates such deployment as placing such an inductive sensor flat against the skin naturally points the axis of the electromagnetic field towards the prosthetic implant. All such components of motion are reported relative to the position of magnetometer 520 as previously described. Microcontroller 500 marshals all of this data for storage and further analysis.

Figure 6A:
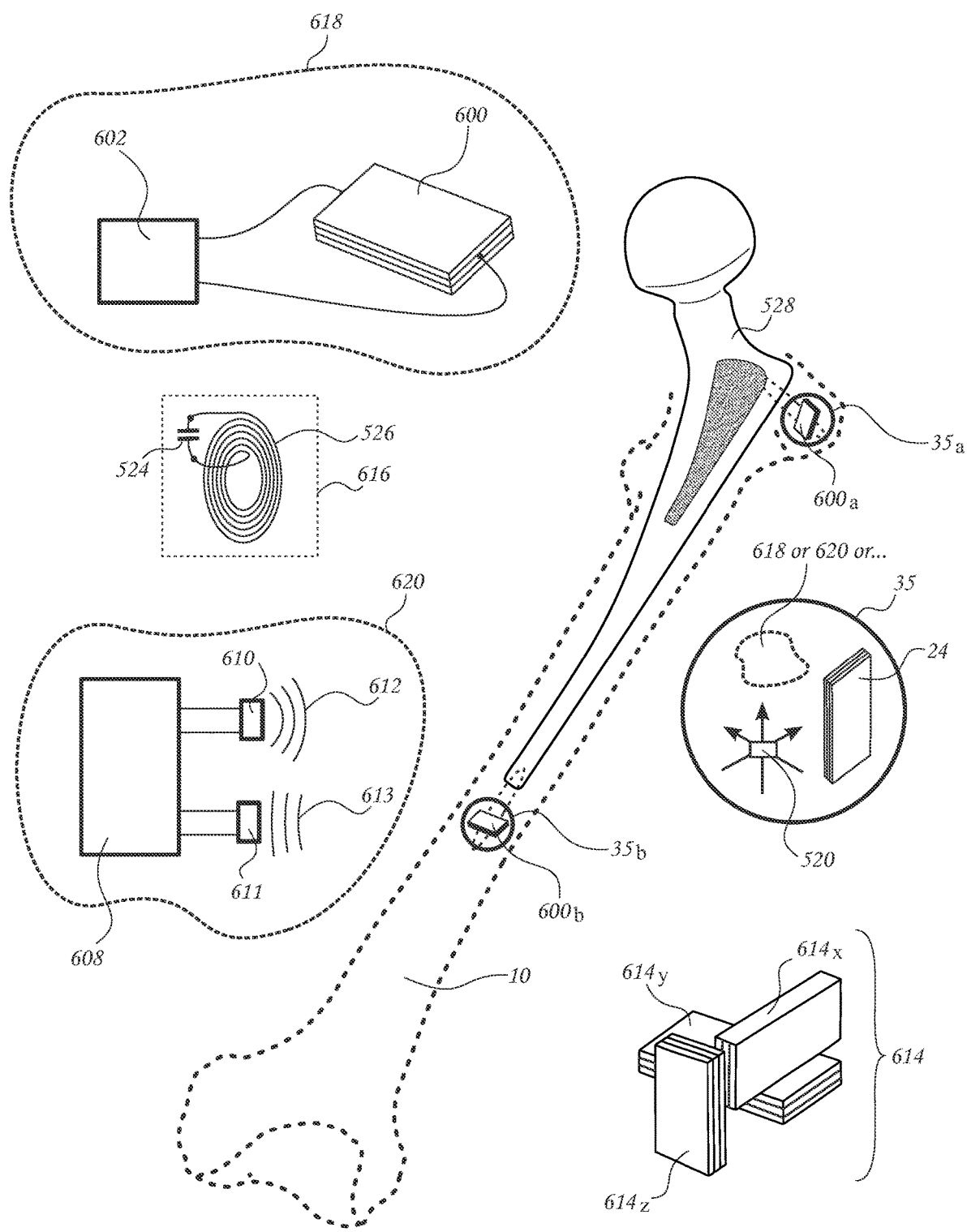
FIG. 6a is a block diagram illustrating an example proximity measuring system to be deployed in vivo and anchored to the femur according to some embodiments of the invention.

Reference is now made to FIG. 6a which shows in abstract form proximity measuring systems to be deployed in vivo and anchored to the femur.

In FIG. 6a an inductance based proximity sensing circuit 618 includes a sensing subsystem 602 which may be of the type described previously as subsystem 530 of FIG. 5, but in this case employing a self-resonant magnetoelectric transducer 600. The LDC1000 integrated circuit conventionally uses a tank circuit 616. If the coil 526 is replaced by magnetoelectric transducer 600 and the capacitor 524 is omitted, the impedance presented to the LDC1000 is quite similar to that of tank circuit 616 and the LDC1000 can make measurements of the effective Rp value as before. However, using a magnetoelectric transducer instead of a tank circuit allows for far greater miniaturization while still operating at the low frequencies desired for in vivo proximity measurements. Also, the quality factor Q of a magnetoelectric transducer is higher than that of a tank circuit allowing for greater measurement sensitivity.

In FIG. 6a, a supersonic Doppler-based proximity sensing system 620 is illustrated, whereby supersonic transceiver 608 driving supersonic transducer 610 which may be a piezoelectric transducer or other suitable type, first emits a sonic signal 612 and then listens to its echo 613 with microphone 611. A single transducer may perform both functions 612 and 613, first emitting a sonic pulse and then switching to a receiving mode and acting as a microphone. Measurement of the relative amplitude, phase and delay between acoustic waves 612 and 613 yields the distance to the target, which in case of a THR would be the femoral implant or the acetabular cup. This sonographic type of position measurement is suitable when a wireless biometric marker 35 positioned quite closely to the prosthesis and a rather high, >1 MHz acoustic frequency can be used permitting high resolution of distance. Measurements using acoustic signals are advantageously not affected by magnetic fields generated by the device due to ongoing power transfer, communication, and marker full position measurements.

FIG. 6a shows femur 10 having femoral implant 528 inserted into the hollowed femoral bone. Two wireless biometric markers 35 are shown with proximal marker 35a fixed to the greater trochanter and distal marker 35b fixed within the femoral bone and inferior to the implant stem. The markers 35a and 35b are shown with magneto electric proximity sensors 600a and 600b.

A biometric marker 35 may have at least the functions shown in the enlarged detail of such a marker 35 in FIG. 6a. Within this detail, marker 35 is shown as including a proximity sensing system 618 or 620, or some other type of proximity sensing system. Marker 35 also includes an energy harvesting and communication transducer 24 of the magnetoelectric type. Marker 35 further includes a suitable magnetoelectric sensor 520 for establishing the full position of the marker relative to an external interface 50. Since proximity sensing, energy harvesting and communication and position measurement can all be achieved with the same type of sensor, it becomes possible to achieve each of these functions one after the other in time by using the same single ME transducer 600 or its circuit equivalent 616 for all of these functions. Such a single transducer may at one time be used to collect energy to power the biometric marker 35 and to communicate with external interface 50 as previously described with reference to FIG. 4, and at another time may serve as the proximity sensing element. Switching the single transducer from one function to another may be achieved by physically connecting all of the necessary circuits to the transducer but electrically activating one at a time the circuits needed to perform first the one function and then the others. The circuits are configured to have a high-impedance state when not activated so they may one at a time share the same electrical connections to the transducer without conflict. It is to be understood that the wireless biometric marker component may use any suitable technologies to realize the three functions of proximity sensing, full position sensing, and communication and power transfer and is not limited in definition to the specific example of achieving these functions given herein.

FIG. 6a also shows a triaxial arrangement of magnetoelectric transducers 614. Such an arrangement of magnetoelectric transducers may be used in place of instances of a single magnetoelectric transducer and provides the advantage of programmable orientation. For example, when using a single magnetoelectric transducer for proximity sensing of the femoral implant, each wireless biometric marker 35 is positioned so that the proximity field emitted by the transducer will interact with the femoral implant. By substituting a triaxial arrangement of magnetoelectric transducers 614x, 614x, and 614z and supplying suitable extra driver channels, it becomes possible to direct the proximity sensing field electronically. This makes the deployment of such markers easier as the surgeon need not be concerned with affixing them in a prescribed orientation relative to the femoral implant.

Figure 6B:
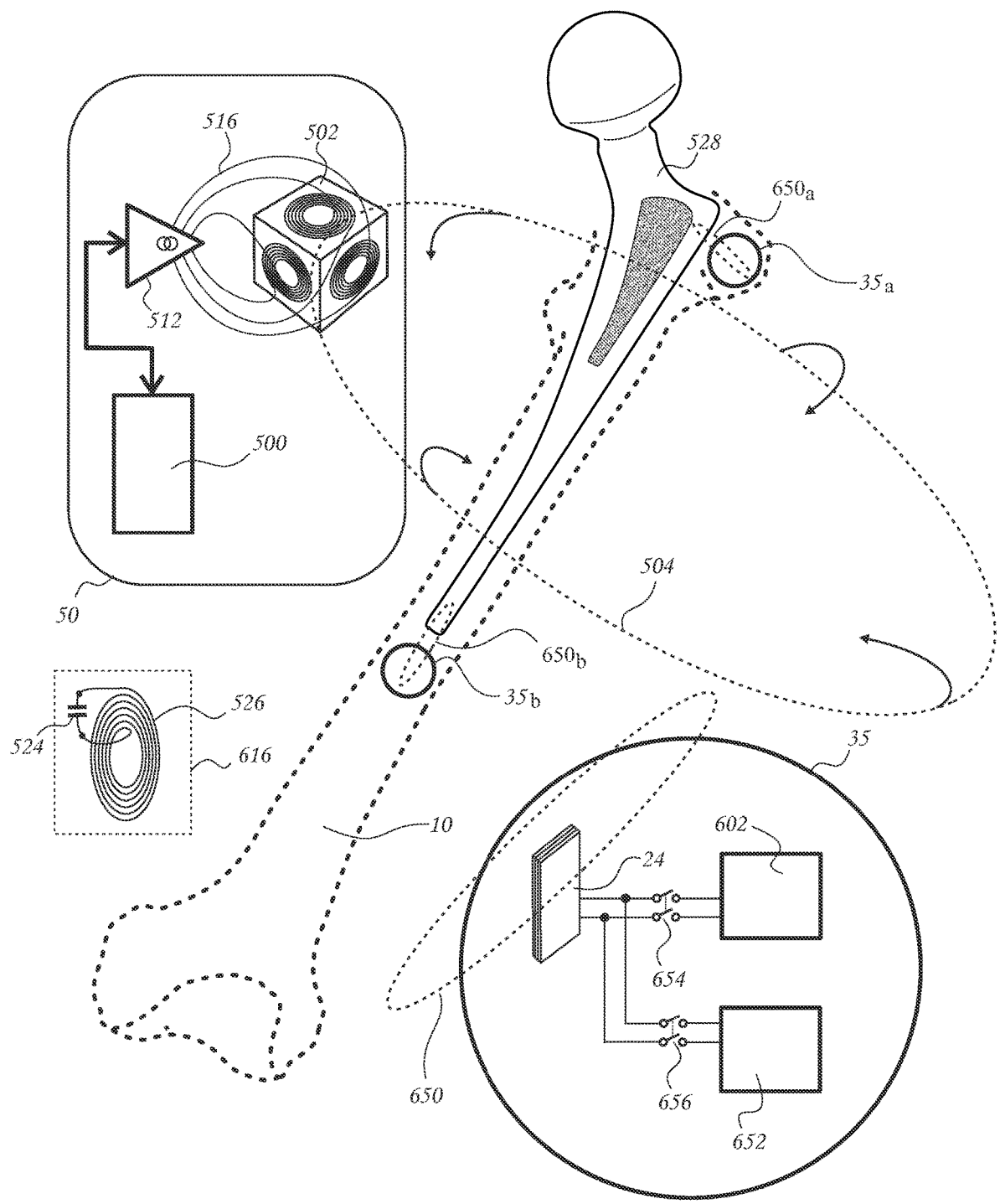
FIG. 6b is a block diagram illustrating an example proximity measuring system having an external sensing interface according to some embodiments of the invention.

FIG. 6b illustrates a preferred embodiment by bringing together previously discussed elements into one possible complete system. Prosthetic implant 528 is shown within femur 10. Biometric markers 35a and 35b are firmly fixed to the femur in proximal and distal positions respectively. The enlarged detail of a biometric marker 35 shows a single magnetoelectric transducer 24 connected via electronic switches 654 and 656 to a circuit 602 and a circuit 652 respectively.

It is understood that magnetoelectric transducer 24 may be substituted by a combination of a coil 526 and capacitor 524 as shown at 616 with similar result although the coil and capacitor would be larger and therefore somewhat less practical than the preferred magnetoelectric transducer 24.

Circuit 602 is a proximity sensor as previously described in the discussion of FIG. 6a. Circuit 652 has been previously described in the discussion of FIG. 4 and includes the energy harvesting system and simultaneous communication system and method shown there and discussed therein as a constituent of biometric marker 35.

Tandem switches 654 and 656 connect transducer 24 to either of circuit 602 or 652 and may be actual electronic switches or may be realized implicitly as a natural function of the circuits 602 and 652 which may present a high impedance when not activated and therefore behave as an open switch when not activated and a closed switch when activated.

External interface 50 has been previously described with reference to FIG. 5 and contains a microcontroller 500 and a three channel driver 512 as previously described, which is connected to triaxial transducer 502. As previously described, such an external interface 50 is capable of emitting a field which may be rotated in to find the best coupling orientation and to convey energy for powering various biometric markers such as 35a and 35b and by discriminating between them according to frequency to communicate data while transmitting power as previously described in connection with FIG. 4.

The system of FIG. 6b may operate by performing a sequence of operations. First, triaxial transducer 502 is energized by driver 512 under the control of microcontroller 500 and discovers each biometric marker 35a and 35b according to their unique frequencies and further discovers the best field 504 orientation for coupling energy. Next, first one and then the other biometric marker is charged up by a charging field 504 emitted by 50, during which time microcontroller 500 may also send instructions to the biometric markers to cause them to perform the intended measurements. During this operation, tandem switch 656 is closed and tandem switch 654 is open. Once this has been done, interface 50 stops emitting a field so as not to interfere with the measurement process about to be performed by the biometric markers. Each biometric marker then executes its instructions and circuit 602 makes a proximity measurement by emitting a field 650 via which magnetoelectric transducer 24 couples to the implant and measures proximity. During this operation tandem switch 654 is closed and tandem switch 656 is open. Finally, switch 654 is opened and 656 is closed, whereupon interface 50 once again becomes active and communicates via field 504 with first one and then the other biometric implant according to their unique frequencies during which communication each biometric implant transmits the proximity data that it discovered during the aforementioned proximity measurement. External interface 50 thus receives the proximity information for further analysis and presentation. The cycle would then be repeated in order to develop additional data for averaging to improve the resolution and to collect data under first a loaded and then unloaded weight condition which conditions can then be compared to extract a measurement indicative of a motion of the implant relative to the biometric markers.

The preceding explanations referencing the FIGS. 1 to 6 provide several alternative apparatus and methods of performing the measurements described herein. The end result is high resolution tracking of the position and orientation of the femoral implant relative to the femur and the acetabular cup implant relative to the pubic bone, and is achieved by making in vivo proximity measurements directly between certain biometric markers and their associated proximate implant components, and also by making measurements between the external measurement and interface 50 and the in vivo markers, and also between interface 50 and the in vivo implant components. By essentially subtracting out the common position terms of the external interface 50 from these measurements, the measurements are transformed to a detailed tracking history of the implant positions and motions relative to the bones they are attached to. From here, further aspects suggest diagnostic procedures and methods of extracting meaningful diagnostic information from the data generated by the system.

Figure 7:
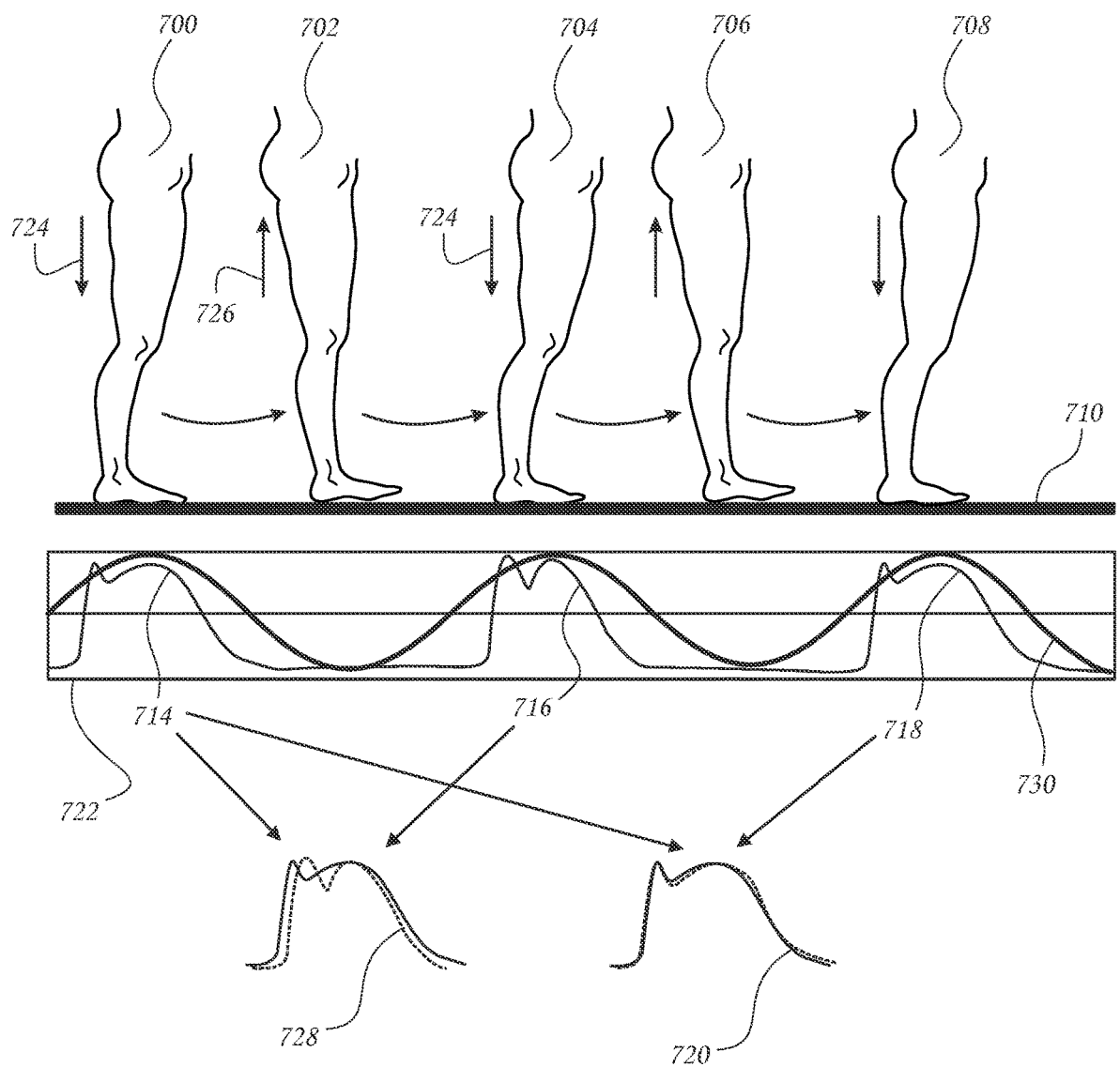
FIG. 7 is a block diagram illustrating an example diagnostic session where data is collected and processed to extract meaningful information according to some embodiments of the invention.

Reference is now made to FIG. 7 which shows an exemplary diagnostic session where data is collected and processed to extract meaningful information. A series of leg positions as presented, beginning with letter position 700 which shows a leg having an implant bearing the weight 724 of the patient. Darkwave 730 illustrates the first harmonic of the gait cycle. Signal 714 is the signal from a sensor responsive to a change in the position of an implant with respect to the patient's bone as reported by interface 50 and derived from a particular wireless biometric marker within the patient's thigh. The first peak of waveform 714 at the 700 position indicates compression of the patient's bone towards the implant due to the transfer of weight onto the heel of the foot. This is followed by the leg lifting off at the toe resulting in a reduced load 726 on the prosthetic and swinging through position 702 without bearing weight towards the next heel touch at position 704 where it once again there is a weight load 724. Three such weight-bearing portions of the gait cycle are shown on the graph.

It is known that the human gait is subject to variation from step to step, yet the same amount of weight is born and removed upon every step. An algorithm is used to gather similar steps from a series of steps so that the timing of weight transfer on and off the foot line up as though the patient's gait were more mechanically inexact than it is. This is shown by contrasting juxtapositions 728 and 720. 728 juxtaposes waveform 714 with the next step which produced waveform 716. These two waveforms although similar do not meet the criteria for selection. In contrast, juxtapositions 720 compares waveform 714 with waveform 718. Here the fit is within the criteria for selection and both waveforms will go on to further processing.

A series of further refinements are applied but have not been illustrated. One refinement is to time stretch or time compress a step waveform such as 718 in a direction that reduces the difference between it and a template waveform. Once the waveform correspondence is thus adjusted, the new waveform is averaged into the current template waveform to produce the next template waveform for comparison with the next step waveform which may be stretched or compressed to better fit the template waveform, and so on through the entire series of gait cycles. During the time-based alignment just described, an amplitude adjustment is also performed where the entire step waveform is multiplied by a coefficient slightly greater than or less than unity in an algorithm designed to minimize the air between a new gait step and the template. At the end of this process of time adjustment and amplitude adjustment there is an array of gait step signals that is averaged into one normalized gait step. Simultaneously with this data from many other sensors is treated the same way. This has the effect of reducing measurement noise and sharpening information bearing data. Those skilled in the mathematics of signal processing will see that there are frequency domain processes that could achieve similar filtering and alignment. An entire gait cycle is thus normalized and passed onward for further analysis and presentation.

Figure 8:
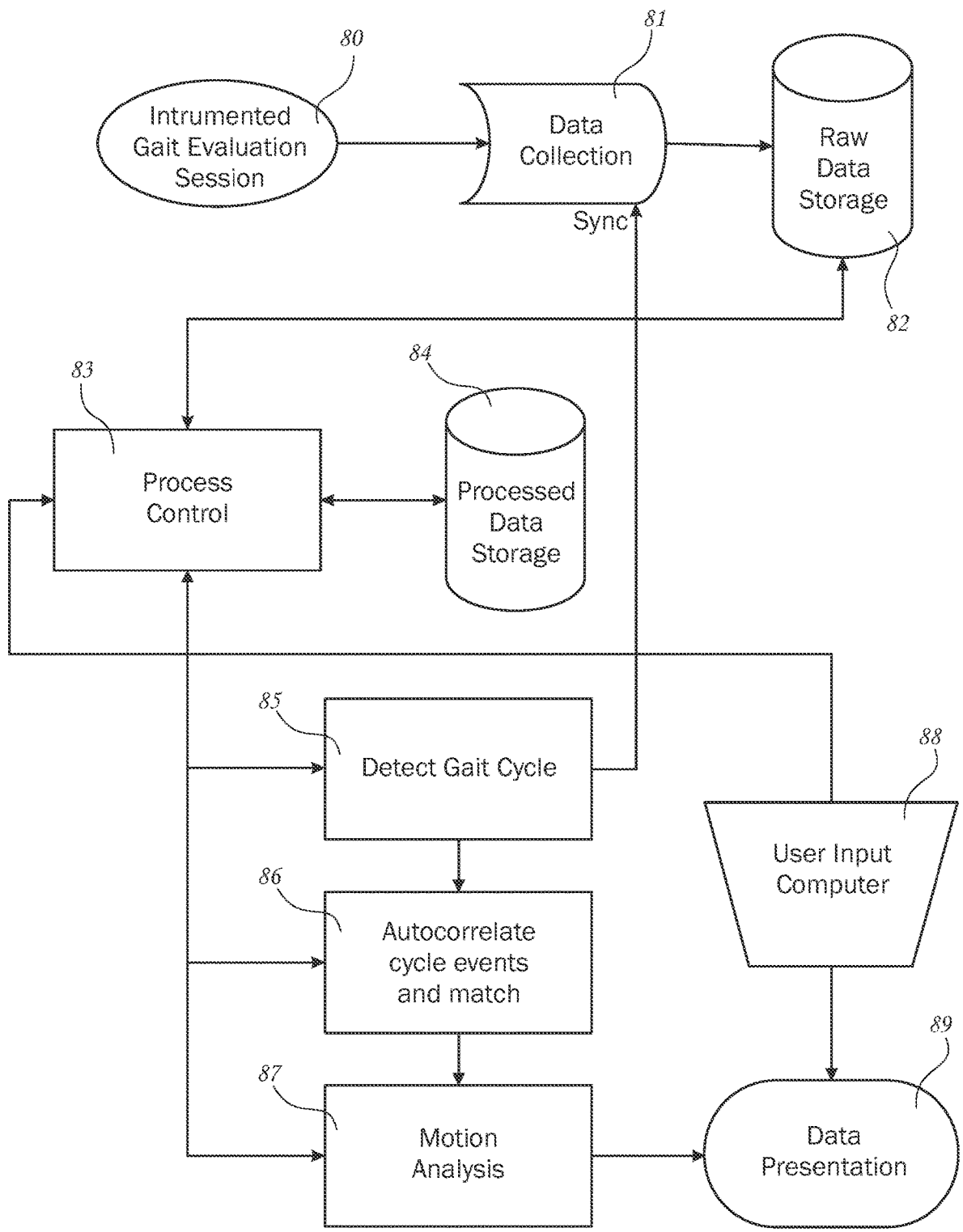
FIG. 8 is a flow diagram illustrating an example process for analyzing prosthesis stability information to determine prosthesis stability according to some embodiments of the invention.

Reference is now made to FIG. 8 which shows a flowchart of a diagnostic process. Instrumented gait evaluation session 80, the details of which have been described in FIGS. 1 to 7, has been completed and the data has been temporarily stored in interface 50. Interface 50 may have collected the data during the course of the diagnostic session, or the data may have been entirely or partially stored within individual wireless biometric markers 35 for transmission after the diagnostic session. In any case, the data ends up being collected by a data collection process 81 and stored in its raw form within storage 82. It must be noted that in physical terms, these events may occur within a computing portion of interface 20, or the data may be conveyed from interface 20 over a network and the processes illustrated in FIG. 8 may take place within any general purpose computing system. Data collected from the sensors is filed in synchronization with the gait cycle as detected by gait cycle detector 85. The inputs to gait cycle detector 85 may originate in the raw data, particularly if data from an accelerometer within wireless biometric markers has been recorded. Such data may be replaced or supplemented by an accelerometer or strain measuring device capable of detecting when the patients heal touches the treadmill and when the patient's toe leaves the surface of the treadmill. Process control 83 and local processed data storage 84 route the data through a variety of signal processing steps which include but are not limited to the auto correlation and matching of one gait cycle to the next, and various motion analysis algorithms such as a Fourier transform for identifying harmonic components of motion, a way to transform for identifying different levels of detail of motion, etc. The reduced data may be manipulated by software such as Matlab and much further experimentation can be done on actual data from real patients to identify the processing algorithms that reveal diagnostically significant data most effectively.

A user input computer 88 may include a screen, a keyboard, devices for accepting and processing voice commands and prewritten scripts, etc. adapted for allowing persons to operate the system. A data presentation aspect receives the analyzed data and presents it in whatever way is deemed best, i.e., on the screen of a computer, in printed form on paper, over a network, etc. The refined data may be presented visually using highlighting colors and or intensities to draw attention to components of motion indicative of implant loosening, unusual twisting of the implant, unusual amounts of compression of the femur measured as a decreasing distance between the proximal and distal biometric markers affixed to the femur, and so forth.

In some embodiments, an empirically-based model of actual clinical experience can be used to determine if the implant is properly placed. For example, a database of distance measurements carried out over time, including a difference over time of the distance measurements and whether the implant became dislodged or had other clinical events, may be used to determine a likelihood that a particular patient's measurements indicate proper placement of the implant or a clinical event, such as slippage or dislodgement. In some embodiments, the measurements may include detecting a first measurement when the implant is substantially free of weight loading and detecting a second measurement when the implant is weight loaded, and whether the implantable device is properly positioned may be based on a difference between the first and second measurement.

Statistical analysis of logged and stored data may be performed in any computing system, including computer networks remote from the sensing system.

EXAMPLES

In a first example embodiment, two or more sensors are placed into the body of a patient during the same surgical procedure in which the THR implant is placed into the body of the patient. The batteries of the sensors are capable of being recharged wirelessly by an external apparatus. The sensors are configured to sense at least one material of the THR implant and the sensors are also configured to sense other sensors. The sensitivity each of the two or more sensors is extremely accurate such that the sensors are able to detect the relative position of an object (e.g., another sensor or the THR implant) in microns.

After a certain period of time post-operation, e.g., two weeks, the sensors are activated by the external apparatus and a baseline measurement of the position of the THR implant is established by determining the relative positions of the sensors and the THR implant. The relative positions are determined by the external apparatus receiving wireless data from each of the one or more sensors and analyzing the sensor data to determine the relative positions. Subsequent to establishing the baseline, future position measurements can be compared to the baseline to determine if the position of the THR implant is changing over time.

Additionally, periodic subject evaluations may also be undertaken. For example, in one embodiment, a subject evaluation involves having the patient walk on a treadmill. While the patient is walking and the weight of the subject (i.e., load) is alternatively transferred onto and transferred off of the THR implant, the sensors are continuously reading out measurements related to the relative position of the THR implant and the other sensors. The sensor data corresponding to the relative positions of the THR implant and the sensors is received by the external apparatus and analyzed to determine if the THR implant is changing position while the subject is transferring load onto and transferring load off of the THR implant.

In a second example embodiment, two or more sensors are placed into the body of a subject surrounding the site of fracture fixation. Analysis of the sensor data from the two or more sensors determines motion at the facture site. When it is determined that the fracture site has a predetermined amount of motion, it is also determined that the fracture has reached a predetermined point in the healing process. Advantageously, motion determination at a fracture site by analysis of the sensor data allows detection of outliers such as delayed union or nonunion of the bone.

The foregoing is illustrative of the present invention and is not to be construed as limiting thereof. Although a few example embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. An implantable position detecting system configured to detect a position of an implantable device with respect to a body structure, the system comprising:
   at least one proximity measuring transducer configured to be implanted on the body structure a distance from the implantable device, the at least one proximity measuring transducer configured to receive electromagnetic energy from an external electromagnetic field generated by an external sensing interface,
   wherein the at least one proximity measuring transducer is configured to emit an emitted signal responsive to the electromagnetic energy and to receive distance information comprising a sensing signal that is responsive to the distance from the at least one proximity measuring transducer implanted on the body structure to the implantable device, wherein the at least one proximity measuring transducer comprises a magnetoelectric transducer having a resonant frequency, and the external sensing interface is configured to transmit energy to the magnetoelectric transducer to drive the magnetoelectric transducer at the resonant frequency in an activation period, and the magnetoelectric transducer is configured to emit the emitted signal as an electromagnetic field and then to sense the electromagnetic field post activation in a sensing period, wherein the external sensing interface or the at least one proximity measuring transducer is further configured to determine a distance from the proximity measuring transducer to the implantable device based on variations in the sensed electromagnetic field due to electromagnetic field interactions with the implantable device.

2. The system of claim 1, wherein the at least one proximity measuring transducer is configured to transmit the distance information to the external sensing interface.

3. The system of claim 1, further comprising a biometric marker, the biometric marker comprising the at least one proximity measuring transducer and at least one additional component selected from the group consisting of an energy storage device, a data storage structure, a microcontroller, and a sensor.

4. The system of claim 3, wherein the at least one additional component comprises a sensor, wherein the sensor is selected from the group consisting of an accelerometer, a magnetometer and a temperature sensor.

5. The system of claim 3, wherein the at least one additional component comprises a microcontroller and a sensor, and wherein the microcontroller is configured to collect data from the at least one proximity measuring transducer or the sensor.

6. The system of claim 3, wherein the at least one additional component comprises an energy storage device, and the external sensing interface is configured to generate an alternating magnetic waveform to drive the magnetoelectric transducer, and the magnetoelectric transducer is configured to convert the alternating magnetic waveform to an electrical signal and to store energy from the alternating magnetic waveform on the energy storage device to thereby provide a wireless power receiver.

7. The system of claim 3, further comprising a transceiver, and wherein the at least one additional component comprises a sensor, a microcontroller, wherein the microcontroller is configured to receive data from the sensor and to send data via the transceiver to the external sensing interface or an external computer system.

8. The system of claim 1, wherein the magnetoelectric transducer comprises an electromagnetic tank circuit having at least one coil element and at least one capacitor element connected in a resonant circuit configuration.

9. The system of claim 1, wherein the implantable device comprises at least one conductive component.

10. The system of claim 1, wherein the external sensing interface comprises at least one external proximity measuring transducer configured to further detect a position of the at least one implantable proximity measuring transducer and the implant.

11. The system of claim 10, wherein the at least one external proximity measuring transducer comprises at least three orthogonal external proximity measuring transducers.

12. The system of claim 11, wherein the at least three orthogonal external proximity measuring transducers comprise magnetoelectric transducers configured to generate an electromagnetic field and to sense an electromagnetic field responsive to a position of the implantable device and the at least one proximity measuring transducer.

13. The system of claim 1, wherein the at least one proximity measuring transducer comprises an ultrasound transducer and an ultrasound receiver, the ultrasound transducer configured to emit an ultrasound signal in a direction toward the implantable device and the ultrasound receiver is configured to receive an echo signal from the implantable device, the at least one proximity measuring transducer being configured to determine a distance to the device responsive to the echo signal.

14. An implantable position detecting system configured to detect a position of an implantable device with respect to a body structure, the system comprising:
  at least one proximity measuring transducer configured to be implanted on the body structure a distance from the implantable device, the at least one proximity measuring transducer configured to receive electromagnetic energy from an external electromagnetic field generated by an external sensing interface,
  wherein the at least one proximity measuring transducer is configured to emit an emitted signal responsive to the electromagnetic energy, and the at least one proximity measuring transducer comprises a magnetoelectric transducer having a resonant frequency, and the external sensing interface is configured to transmit energy to the magnetoelectric transducer to drive the magnetoelectric transducer at the resonant frequency in an activation period, and the magnetoelectric transducer is configured to emit the emitted signal as an electromagnetic field and then to sense the electromagnetic field post activation in a sensing period; and
  wherein the at least one proximity measuring transducer is a component of a proximity sensing system configured to receive a sensing signal that is responsive to the distance from the at least one proximity measuring transducer implanted on the body structure to the implantable device;
  wherein the external sensing interface or the at least one proximity measuring transducer is further configured to determine a distance from the proximity measuring transducer to the implantable device based on variations in the sensed electromagnetic field due to electromagnetic field interactions with the implantable device.

15. The system of claim 14, wherein the sensing signal comprises the electromagnetic field sensed post activation in the sensing period.

16. The system of claim 15, further comprising an energy storage device, and the external sensing interface is configured to generate an alternating magnetic waveform to drive the magnetoelectric transducer, and the magnetoelectric transducer is configured to convert the alternating magnetic waveform to an electrical signal and to store energy from the alternating magnetic waveform on the energy storage device.

17. The system of claim 14, wherein at least a portion of the proximity sensing system is provided as part of the external sensing interface.

* * * * *